United States Patent [19]
Leonardi

[11] Patent Number: 5,644,800
[45] Date of Patent: *Jul. 8, 1997

[54] SPORTS PAD FOR EYEWEAR FRAMES

[75] Inventor: Peter F. Leonardi, Gloversville, N.Y.

[73] Assignee: Halo Sports and Safety, Inc., Gloversville, N.Y.

[*] Notice: The term of this patent shall not extend beyond the expiration date of Pat. No. 5,495,623.

[21] Appl. No.: 246,247

[22] Filed: May 19, 1994

Related U.S. Application Data

[63] Continuation-in-part of Ser. No. 195,468, Feb. 14, 1994, Pat. No. 5,495,623.

[51] Int. Cl.$^6$ ............................................. A61F 9/02
[52] U.S. Cl. ................................. 2/431; 2/439; 2/440
[58] Field of Search .............................. 2/431, 439, 440, 2/441, 442, 443, 454, 9; 351/87, 138

[56] References Cited

U.S. PATENT DOCUMENTS

| | | | |
|---|---|---|---|
| 1,288,140 | 12/1918 | Nixson | 2/439 |
| 1,306,357 | 6/1919 | Shindel | 2/439 |
| 1,344,474 | 6/1920 | Beattey | 351/102 |
| 1,754,694 | 4/1930 | Neuwirth | 2/440 |
| 2,406,608 | 8/1946 | Joyce | 2/450 |
| 2,504,524 | 4/1950 | Hayward | 2/452 |
| 2,545,428 | 3/1951 | Liautaud | 2/452 |
| 2,755,803 | 7/1956 | Dorsey | 2/426 |
| 2,918,676 | 12/1959 | Matheson | 2/440 |
| 3,027,562 | 4/1962 | Widenor | 2/430 |
| 3,584,939 | 6/1971 | Olson et al. | 351/132 |
| 3,993,403 | 11/1976 | Brown | 351/178 |
| 4,176,410 | 12/1979 | Mathhias | 2/436 |
| 4,222,640 | 9/1980 | Bononi | 351/83 |
| 4,229,837 | 10/1980 | Solari | 2/439 |
| 4,279,040 | 7/1981 | Garofalo | 2/428 |
| 4,367,561 | 1/1983 | Solari | 2/439 |
| 4,621,378 | 11/1986 | Hatchman | 2/431 |
| 4,688,272 | 8/1987 | Leonardi | 2/431 |
| 5,016,293 | 5/1991 | Lickle | 2/436 |
| 5,033,837 | 7/1991 | Leonardi | 351/121 |
| 5,042,094 | 8/1991 | Sadowsky | 2/439 |
| 5,046,198 | 9/1991 | Hunnebeck | 2/440 |
| 5,137,342 | 8/1992 | Jannard et al. | 351/123 |
| 5,138,723 | 8/1992 | Bollé | 2/430 |
| 5,184,354 | 2/1993 | Alfaro et al. | 2/425 |
| 5,339,119 | 8/1994 | Gardner | 2/431 X |

FOREIGN PATENT DOCUMENTS

| | | | |
|---|---|---|---|
| 496831 | 11/1919 | France | 2/431 |
| 1535556 | 7/1968 | France . | |
| 506357 | 12/1954 | Italy | 2/431 |
| 215693 | 5/1924 | United Kingdom . | |
| 8600012 | 1/1986 | WIPO | 351/114 |

*Primary Examiner*—Peter Nerbun
*Attorney, Agent, or Firm*—Roylance, Abrams, Berdo & Goodman, L.L.P.

[57] ABSTRACT

A sports pad for substantially covering certain exposed areas of an eyewear frame to prevent facial cutting from the hard, rigid eyewear frame. The sports pad is preferably formed of a resilient, flexible elastomeric material. The sports pad is removably coupled to the eyewear frame by stretching the sports pad relative the eyewear frame. Preferably, the sports pad includes a pair of temple cushions and a nose cushion. The sports pad can be constructed to cover either eyewear with frameless lenses, partially frameless lenses, or framed lenses. In some embodiments, substantially the entire front portion of the eyewear is covered by the sports pad, while in other embodiments, only the peripheral edge of the front portion of the eyewear is covered.

12 Claims, 16 Drawing Sheets

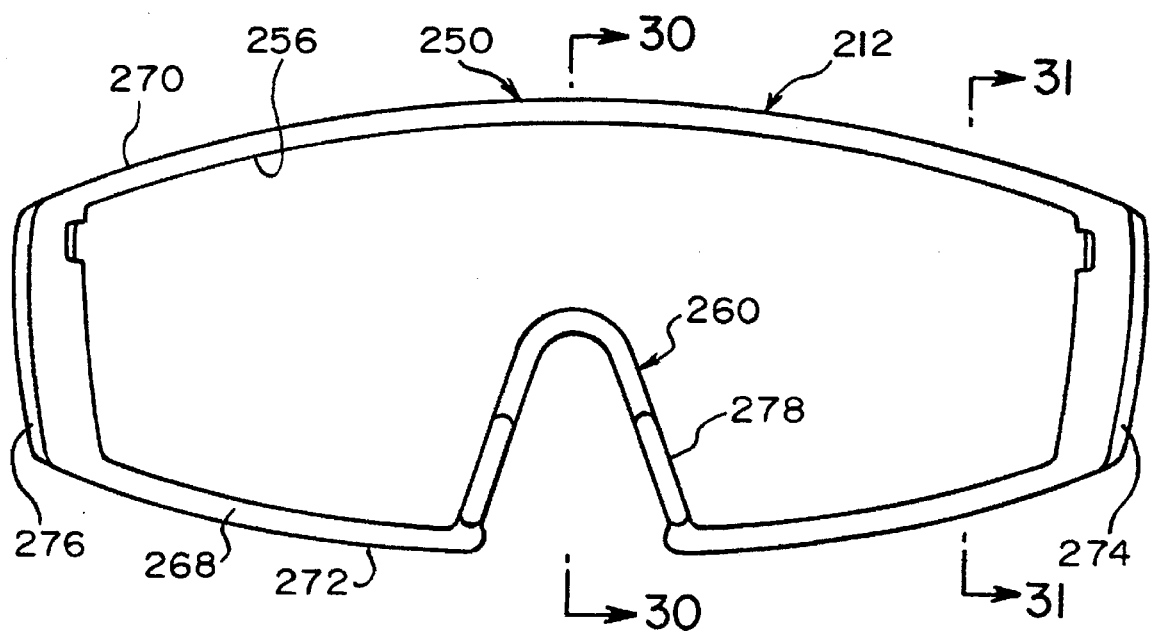
FIG. 29
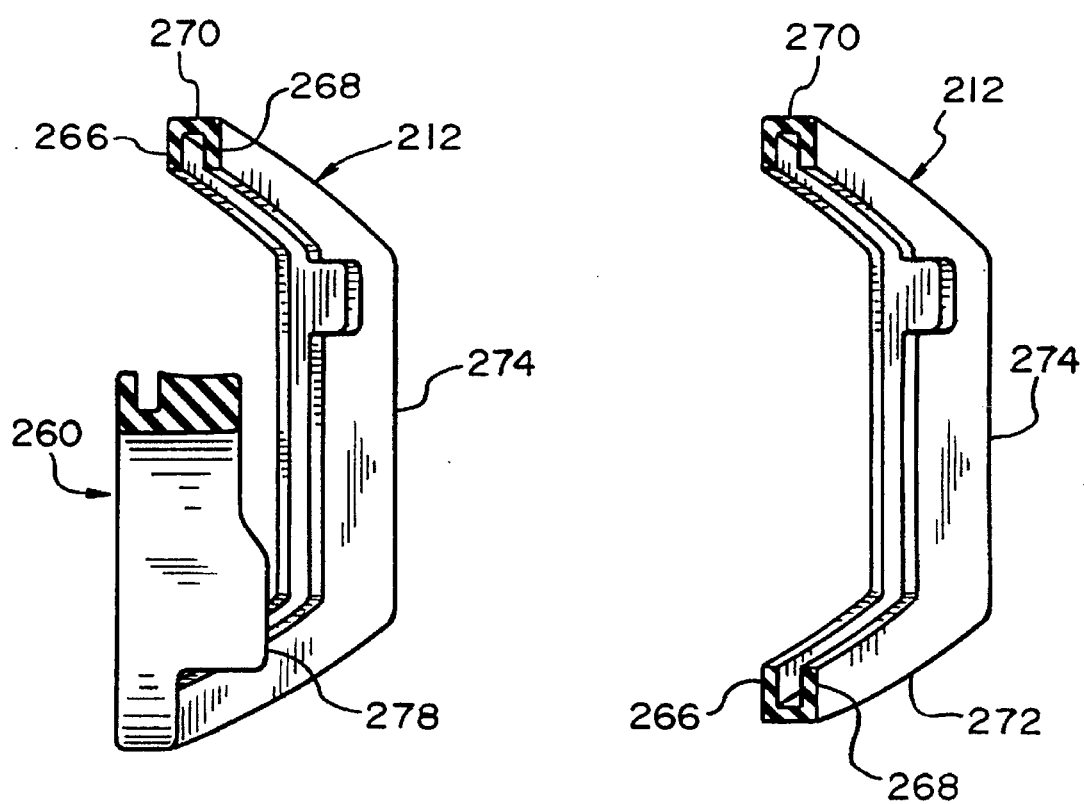
FIG. 30
FIG. 31

SPORTS PAD FOR EYEWEAR FRAMES

RELATED APPLICATION

This application is a continuation-in-part application of Ser. No. 08/195,468 filed Feb. 14, 1994, now U.S. Pat. No. 5,495,623.

FIELD OF THE INVENTION

This invention relates to sports pads for covering eyewear frames. More specifically, the invention relates to a soft, resilient pad for covering sports eyeglasses for use in sporting activities to prevent eye injury to a player from a ball, equipment, hands, or the like. The sports pad is removably coupled to the rigid frame of the eyeglasses for substantially covering the entire exposed area of the frame to prevent facial cutting.

BACKGROUND OF THE INVENTION

In a large number of sporting activities, such as tennis, hand ball, squash, racket ball, basketball, soccer, football, hockey, and other sporting activities in which there is fast movement of players and the use of a ball or other physical contact, there exists a continuing danger of a participant being struck in the eye by the ball, equipment or hand of an opponent. This can result in severe injury or even, in some cases, loss of an eye.

Thus, a variety of different types of protective eyewear has been developed for each of the variety of sporting activities. Generally, the protective eyewear are formed as either eyeglasses or goggles. Many of these prior protective eyeglasses suffer from one or more deficiencies. For example, some protective eyewear are very uncomfortable to wear since they are made of a very hard rigid plastic. Other protective eyewear is heavy and cumbersome to wear, which causes the wearer substantial discomfort during participation in the sporting event.

Accordingly, most protective eyewear is now constructed of lightweight, hard, rigid plastic with pads fixedly coupled thereto. For example, U.S. Pat. No. 4,688,272 to Leonardi discloses sports frames constructed of a lightweight plastic with a pair of temple pads and a nose pad fixedly coupled thereto. However, the sports frames disclosed by the Leonardi patent and many other prior eyeglasses do not provide easily removable pads which can be replaced when they wear out, or which can be changed with other pads of a different color to provide a different fashionable look.

Moreover, many prior eyeglasses do not provide sufficient pad to cover substantially all areas of the frame which are exposed to the wearer. Accordingly, the wearer of such eyeglasses is quite often cut by the frames, when the frames are struck by an object. Some eyeglasses have been manufactured with additional pads or padding in an attempt to overcome this problem. However, these eyeglasses present other problems or disadvantages. Namely, the padding often interferes with the installation of the lenses into the frame of the eyeglasses, since the optician cannot heat the frame without damaging the padding. Also, if the padding is molded onto the frame of the eyeglasses, then both the padding and frames are lost if either part is flawed and rejected.

Other examples of various prior devices relating to protective eyewear are disclosed in U.S. Patents: U.S. Pat. No. 1,288,140 to Nixson; U.S. Pat. No. 1,344,474 to Beattey; U.S. Pat. No. 1,754,694 to Neuwirth; U.S. Pat. No. 2,406,608 to Joyce; U. S. Pat. No. 2,504,524 to Hayward; U.S. Pat. No. 2,545,428 to Liautaud; U.S. Pat. No. 2,755,803 to Dorsey; U.S. Pat. No. 3,584,939 to Olson et al; U.S. Pat. No. 3,993,403 to Brown; U.S. Pat. No. 4,176,410 to Mattbias; U.S. Pat. No. 4,222,640 to Bononi; U.S. Pat. No. 4,229,837 to Solari; U.S. Pat. No. 4,367,561 to Solari; U.S. Pat. No. 5,016,293 to Lickle; U.S. Pat. No 5,033,837 to Leonardi; U.S. Pat. No. 5,046,198 to Hunnebeck; U.S. Pat. No. 5,137,342 to Jannard et al; U.S. Pat. No. 5,138,723 to Bolle and U.S. Pat. No. 5,184,354 to Alfaro et al.

In view of the above, it is apparent that there exists a need for protective eyewear which is comfortable to wear and can be used in almost any sporting activity. This invention addresses these needs in the art, along with other needs which will become apparent to those skilled in the art once given this disclosure.

SUMMARY OF THE INVENTION

Accordingly, an object of the invention is to provide a soft, resilient connector pad for covering portions of a rigid eyewear frame or lens which are exposed to the wearer's face.

Another object of the invention is to provide a sports pad for eyeglasses which can be easily replaced.

Another further object of the invention is to provide a sports pad that is simple to manufacture, aesthetically pleasing, and not bulky.

Yet another object of the invention is to provide a pair of sports eyeglasses which are comfortable to wear.

The foregoing objects are basically attained by providing a removable sports pad for covering at least certain exposed peripheral edges of eyewear with a front portion and a pair of temple portions, comprising: a front wall for removably overlying certain forwardly facing areas of the eyewear; a rear wall spaced from the front wall for removably overlying certain rearwardly facing areas of the eyewear and for removably receiving the eyewear therebetween; and a peripheral wall coupled between the front and rear walls for removably overlying certain peripheral edges of the eyewear; each of said front, rear and peripheral walls of said pad being constructed of a soft, stretchable, resilient material for removably retaining the pad on the eyewear and being shaped to overlie at least the peripheral edges of the eyewear along its lens.

The foregoing objects are also basically attained by a sports eyewear for eye protection, comprising: a substantially rigid eyewear frame having a front portion with at least one lens, a first temple portion being coupled to a first end of said front portion of said frame, and a second temple portion being coupled to a second end of said front portion of said frame; and a soft elastomeric pad removably coupled to said frame for covering at least certain exposed areas of said frame, said pad including a front wall for removably overlying certain forwardly facing areas of said eyewear; a rear wall spaced from said front wall for removably overlying certain rearwardly facing areas of said eyewear and for removably receiving said eyewear therebetween; and a peripheral wall coupled between said front and rear walls for removably overlying certain peripheral edges of said eyewear; each of said front, rear and peripheral walls of said pad being constructed of a soft, stretchable, resilient material for removably retaining said pad on said eyewear and being shaped to overlie at least portions of the peripheral edges of the eyewear along said at least one lens.

Other objects, advantages and salient features of the invention will become apparent from the following detailed description, which, taken in conjunction with the annexed drawings, discloses several preferred embodiments of the invention.

BRIEF DESCRIPTION OF THE DRAWINGS

Referring now to the drawings which form part of this original disclosure:

FIG. 29 is a rear elevational view of the sports pad illustrated in FIGS. 24 and 26–28 in its original unstretched state prior to be stretched over the sports eyewear frames as shown in FIG. 25;

FIG. 30 is a cross-sectional view of the unstretched sports pad of FIGS. 24 and 26–30 taken along section line 30-30 of FIG. 29;

FIG. 31 is a cross-sectional view of the unstretched sports pad of FIGS. 24 and 26–30 taken along section line 31—31 of FIG. 29;

DETAILED DESCRIPTION OF THE INVENTION

Figure 1:
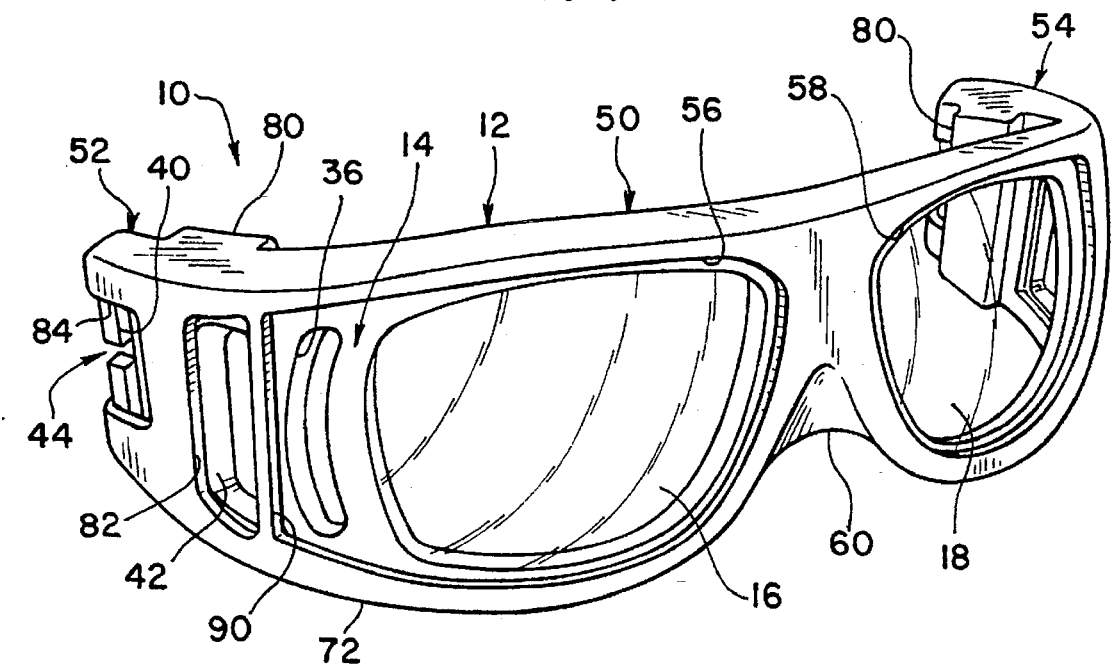
FIG. 1 is a front perspective view of a pair of conventional sports eyeglasses covered by a sports pad in accordance with a first embodiment of the present invention.
Figure 2:
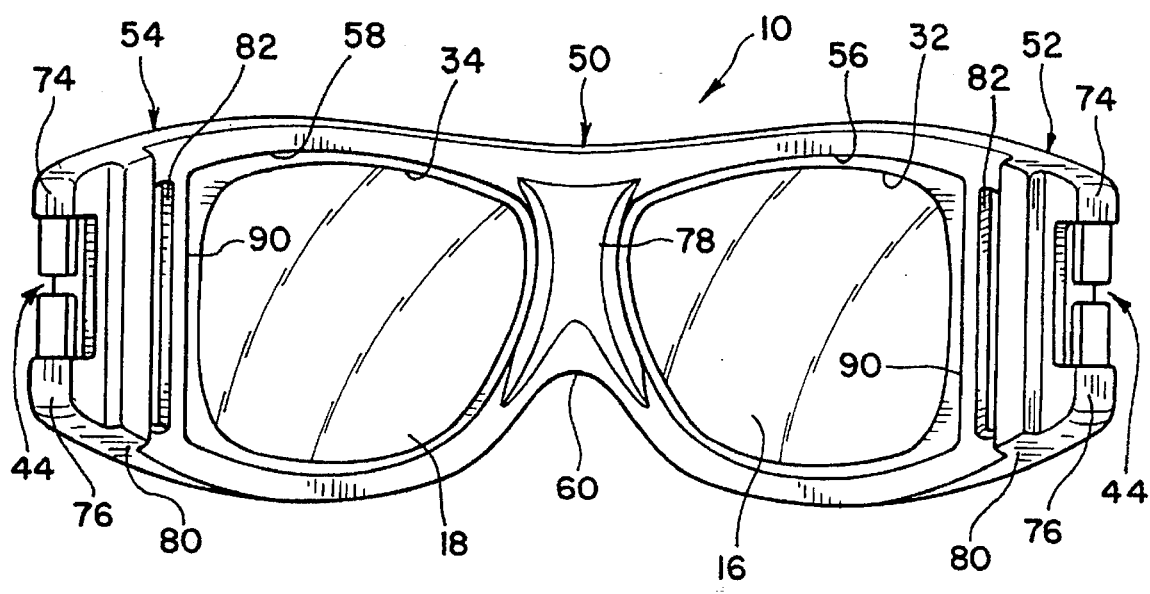
FIG. 2 is a rear elevational view of the eyeglasses and sports pad illustrated in FIG. 1 in accordance with the present invention.
Figure 3:
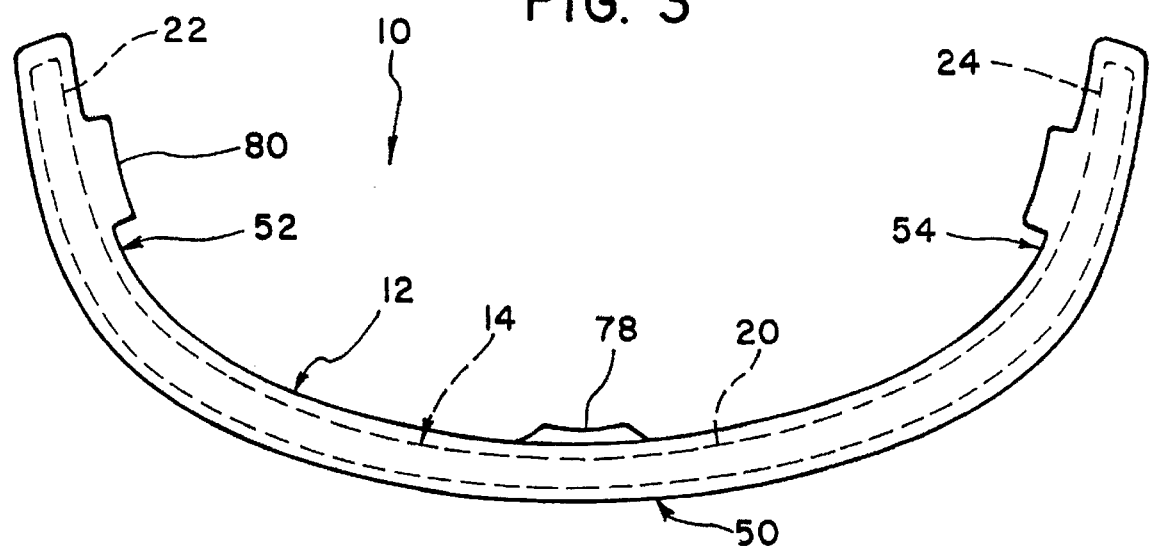
FIG. 3 is a top plan view of the eyeglasses and sports pad illustrated in FIGS. 1 and 2 in accordance with the present invention.
Figure 4:
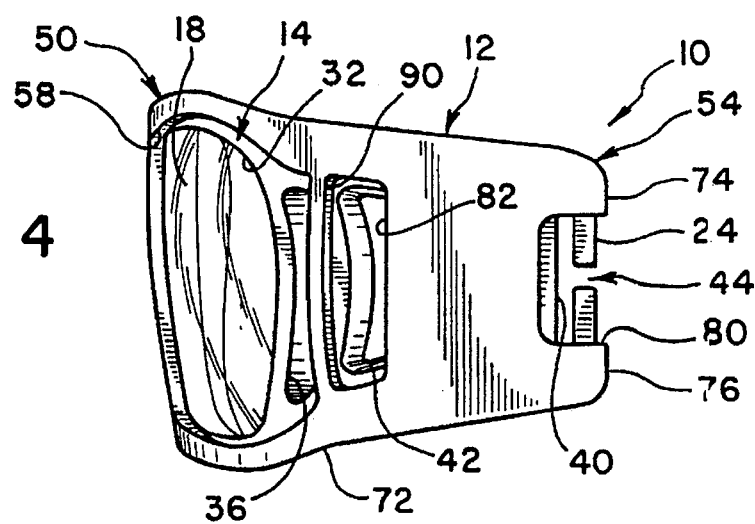
FIG. 4 is a side elevational view of the eyeglasses and sports pad illustrated in FIGS. 1–3.

Referring initially to FIGS. 1–4, a pair of sports eyeglasses or eyewear 10 with a sports pad 12 coupled to a frame 14 of eyewear 10 is illustrated in accordance with a first embodiment of the present invention. Sports pad 12 is removably coupled to frame 14, and constructed of a soft, flexible, resilient rubber material which allows pad 12 to be stretched over frame 14.

Pad 12 covers substantially all exposed areas of frame 14 which can cause facial cutting when the eyeglasses 10 are struck by an object. Accordingly, the soft, rubber material of pad 12 is preferably transversely compressible to compress between the wearer's head and eyeglasses upon the eyeglasses 10 being struck by an object. In other words, pad 12 will prevent facial cutting from the hard frame 14 of eyeglasses 10 by absorbing a portion of the force exerted on the wearer's head from an object striking eyeglasses 10.

Preferably, pad 12 is injection molded from a thermoplastic elastomer as a one-piece, unitary member, i.e., constructed of one substantially homogeneous piece of material, not including separate but joined elements. Frame 14, on the other hand, is constructed of a hard material, and includes a pair of lenses 16 and 18 fixedly coupled thereto.

As seen in FIGS. 1–4, pad 12 substantially covers and encompasses all exposed areas of frame 14 to prevent facial cutting from the hard frame 14 during impact with an object. A particularly suitable material for pad 12 is a very soft, elastomeric material with a durometer of approximately 13 ASTM A Shore to approximately 20 ASTM A Shore, such as the elastomer sold under the trademark Elastalloy which is an elastomeric derivative of the elastomer manufactured and sold by Shell Chemical Company under the trademark Kraton. Basically, the Elastalloy and Kraton elastomers are comprised of a block copolymer of butadiene, isoprene and styrene.

Pad 12 can be removably installed over frame 14 by stretching the resilient, rubber material of pad 12 over rigid frame 14 of eyeglasses 10. Accordingly, pad 12 can be easily replaced when worn out or changed to a different color pad. For example, pad 12 can be sold separately in a variety of colors, or sold as a kit containing a pair of protective eyeglasses 10 and a plurality of pads in a variety of colors.

Frame 14 is a conventional protective frame which is constructed of a hard, rigid material. It will be apparent to those skilled in the art from this disclosure that a variety of frames of other configurations can be used in conjunction with the present invention by modifying pad 12 to properly fit the particular configuration of the particular frames being used.

Figure 5:
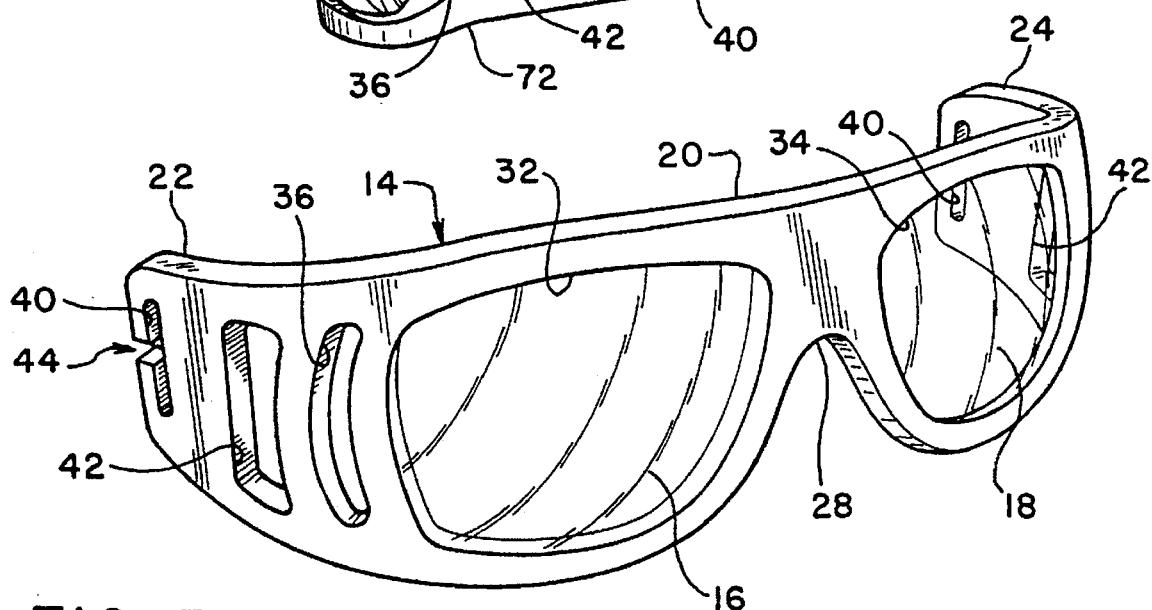
FIG. 5 is a front perspective view of the conventional prior art sports eyeglasses illustrated in FIGS. 1–4 with the sports pad removed.

As seen in FIG. 5, frame 14 is preferably integrally molded as a one-piece, unitary frame having a curved front portion 20, a first end or temple portion 22 extending rearwardly from one end of front portion 20, and a second end or temple portion 24 extending rearwardly from the other end of front portion 20. The integrally molded frame 14 can be constructed of any material, but is advantageously constructed of a lightweight, moldable, shatterproof polymeric material, such as polycarbonate, propionate, cellulose acetate, nylon or butyrate. Frame 14 is illustrated in the figures as being constructed of an opaque material which can be any color. However, it will be apparent from this disclosure that frame 14 can be constructed of a transparent material which is either clear or colored.

Front portion 20 of frame 14 includes a centrally located nose area 28 forming a curved recess for receiving a wearer's nose, and a pair of apertures 32 and 34 for retaining lenses 16 and 18 therein. In particular, each of the apertures 32 and 34 preferably has a peripheral recess for retaining lenses 16 and 18, respectively, therein. Lenses 16 and 18 can be either refractive, i.e., prescription lenses, or non-refractive, i.e., non-prescription lenses, as needed. Of course, when using non-prescription lenses, lenses 16 and 18 can be integrally formed with frame 14 as a one-piece, unitary member with frame 14 and lenses 16 and 18 being formed of a clear or colored transparent plastic material. Alternatively, apertures 32 and 34 can be interconnected for receiving a single lens which is either refractive or non-refractive.

Optionally, front portion 20 of frame 14 can have a pair of ventilation openings 36 and 38 to provide adequate circulation of air between frame 14 and the wearer's face. In particular, ventilation opening 36 is positioned between first end portion 22 and aperture 32, and ventilation opening 38 is positioned between second end portion 24 and aperture 34.

As particularly seen in FIG. 5, first end portion 22 and second end portion 24 are integrally molded with front portion 20 and extends approximately 1.5 inches rearwardly from the ends of front portion 20. First end or temple portion 22 and second end or temple portion 24 are substantially identical, and thus, only first end portion 22 will be discussed and illustrated in detail.

First end portion 22 has a strap slot 40 at its free end and an optional ventilation opening 42 at its other end. The forward edge of ventilation opening 42 demarks the transition point between frame front 20 and first end portion 22. Ventilation opening 42 also ensures adequate circulation of air between the wearer's face and frame 14 of the eyeglasses 10 with pad 12 thereon.

Strap slot 40 extends substantially vertically when eyeglasses 10 are worn by a wearer, and receives a conventional headband or strap (not shown) for securing the eyeglasses 10 to the wearer's head. An access slot 44 extends substantially perpendicularly from the midpoint of strap slot 40 to the free end of first end portion 22 to provide easy installation of the headband or strap (not shown) into strap slot 40 in a conventional manner.

Referring now to FIGS. 8–11, pad 12 is constructed as a one-piece, unitary member, and includes a front portion 50 for overlying and encompassing substantially all of the exposed areas of front portion 20 of frame 14, and first and second end or temple portions 52 and 54 for substantially overlying and encompassing all of the exposed areas of end portions 22 and 24 of frame 14, respectively. Accordingly, pad 12 fits over the hard, rigid material of frame 14 to provide a cushioning effect on the top, bottom, front and rear sides of frame 14 by substantially covering all of the exposed surfaces of frame 14.

Pad 12 is dimensioned smaller than frame 14 so that pad 12 can be installed and removed by stretching pad 12 onto frame 14. The stretchability and resiliency of pad 12 permits a single pad 12 to be used on a plurality of different sizes of frames. In other words, a plurality of sizes of frames 14 can be fitted with the same pad 12 formed from a single mold due to the large degree of elasticity of pad 12.

Front portion 50 of pad 12 includes a pair of lens apertures 56 and 58, and a nose portion 60 positioned between lens apertures 56 and 58. Apertures 56 and 58, in their normal unstretched state, are preferably nonuniformly smaller than apertures 32 and 34 of frame 14 to provide a secure fit about the frame 14. In particular, apertures 56 and 58 each has an upper concaved portion 62 and a lower concaved portion 64 for engaging and gripping the portion of frame 14 about apertures 32 and 34 of frame 14. The non-uniformity of front portion 50 of pad 12 depends upon the size and shape of frame 14. In other words, the precise shape of pad 12 will vary depending upon the shape of frame 14.

Figure 10:
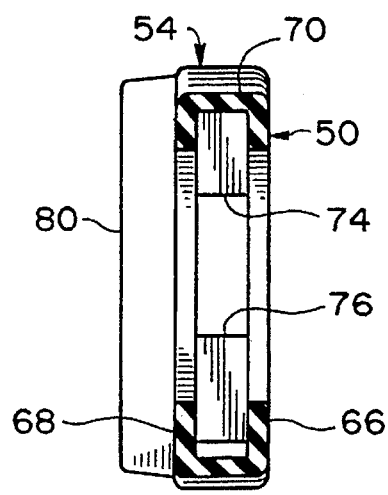
FIG. 10 is a cross-sectional view of the unstretched sports pad of FIGS. 1–4 and 6–9 taken along section line 10—10 of FIG. 9.
Figure 11:
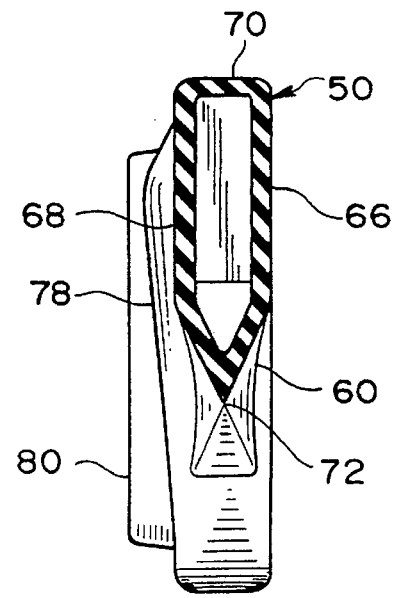
FIG. 11 is a cross-sectional view of the unstretched sports pad of FIGS. 1–4 and 6–10 taken along section line 11—11 of FIG. 9.

As seen in FIGS. 10 and 11, front portion 50 of pad 12 is formed by a front wall 66, a rear wall 68, a top peripheral wall 70 and a bottom peripheral wall 72. Front wall 66, rear wall 68, top peripheral wall 70 and bottom peripheral wall 72 extend from front portion 50 to form part of end portions 52 and 54. End portions 52 and 54 also include a pair of end walls 74 and 76 which together with front wall 66, rear wall 68, top wall 70 and bottom wall 72 form a pair of end pockets for engaging end portions 22 and 24 of frame 14. These end pockets of pad 12 are stretched over end portions 22 and 24 to place pad 12 under longitudinal tension as well as transverse tension. Accordingly, pad 12 is elastically stretched and thereby retained on frame 14 to limit shifting of pad 12 on frame 14.

Figure 8:
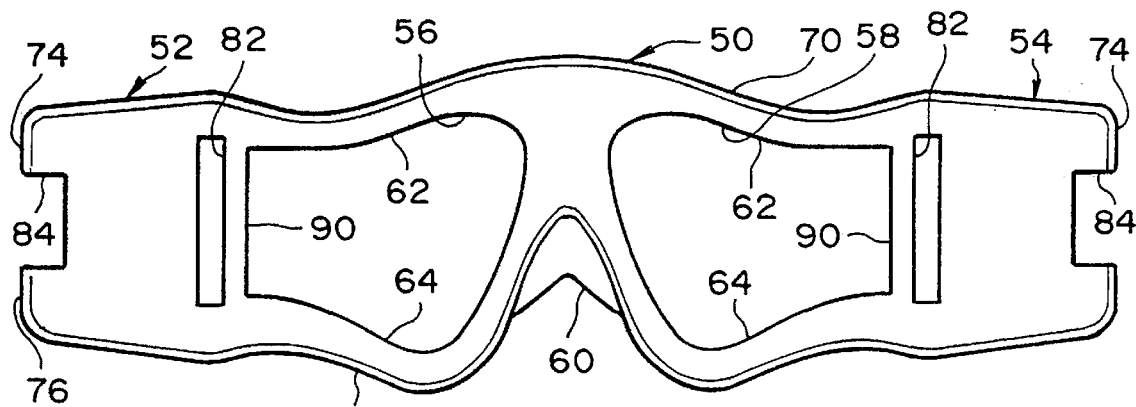
FIG. 8 is a front elevational view of the sports pad illustrated in FIGS. 1–4, 6 and 7 in its original unstretched state.
Figure 9:
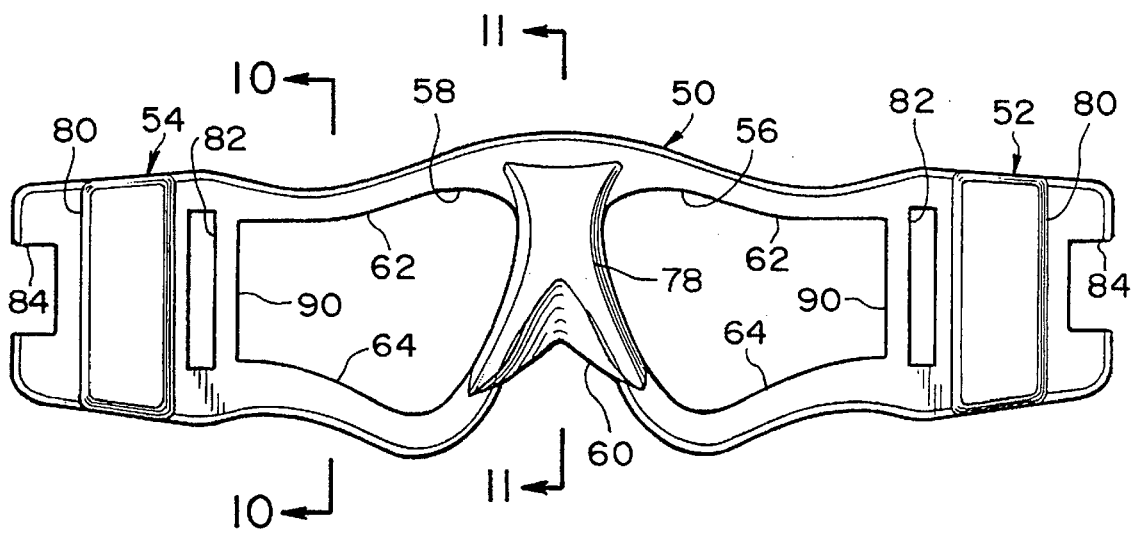
FIG. 9 is a rear elevational view of the sports pad illustrated in FIGS. 1–4 and 6–8 in its original unstretched state.

When pad 12 is in its unstressed state as shown in FIGS. 8 and 9, front wall 66 is parallel to and spaced from rear wall 68 to receive frame 14 therebetween. Preferably, the distance between front wall 66 and rear wall 68 is slightly greater than the thickness of frame 14 in its unstressed state. Of course, the distance between front wall 66 and rear wall 68 can be smaller than or the same size as the thickness of frame 14. Preferably, when pad 12 is stretched onto frame 14, the distance between rear front wall 66 and rear wall 68 will decrease to elastomerically grip frame 14.

Top peripheral wall 70 and bottom peripheral wall 72 extend substantially perpendicularly between front wall 66 and rear wall 68 for engaging the upper and lower edges of frame 14, respectively. End walls 74 and 76, together with front wall 66, rear wall 68, top peripheral wall 70 and bottom peripheral wall 72 of end portions 52 and 54, form a pair of end pockets for engaging the ends of frame 14. Walls 66, 68, 70, 72, 74 and 76 preferably have a thickness ranging from about 0.075 inch to about 0.090 inch.

Nose portion 60 includes a nose cushion 78 which extends outwardly from rear wall 68 between apertures 56 and 58. Nose cushion 78 provides additional padding between the wearer's nose and the nose area 28 of frame 14. In particular, nose cushion 78 is contoured to engage the wearer's nose and has a variable thickness ranging from about 0.075 inch to about 0.220 inch. Of course, nose cushion 78 can be made thicker or smaller as needed or desired.

First and second end or temple portions 52 and 54 are substantially identical, and thus, only first end or temple portion 52 will be discussed herein. First end or temple portion 52 includes a temple cushion 80, a ventilation opening 82 positioned between temple cushion 80 and aperture 56 of pad 12, and a cutout 84 for exposing strap slot 40 and access slot 44 to accommodate a headband or strap (not shown) therein.

Temple cushion 80 extends outwardly from rear wall 68 of pad 12 for engaging the wearer's temple. Preferably, temple cushion 80 extends outwardly from rear wall 68 by a distance approximately 0.490 inch.

Pad 12 has four bars 90 with one of the bars 90 being located between each of the ventilation openings 82 and the apertures 56 and 58 of the pad. Optionally, pad 12 may be constructed without some or all of the ventilation openings 82. For example, the two bars 90 on rear wall 68 of pad 12 may be removed so that apertures 56 and 58 of the rear wall are larger than apertures 56 and 58 of the front wall 66 of pad 12. In other words, apertures 56 and 58 of the rear wall 68 would encompass ventilation openings 82 when the two bars 90 on the rear wall 68 are removed.

Ventilation openings 82 are sized and positioned to coincide with ventilation openings 42 of frame 14 when pad 12 is coupled to frame 14. Accordingly, this arrangement allows for adequate ventilation between the eyeglasses 10 and the wearer without exposing the hard plastic to the wearer's face. In other words, pad 12 provides adequate cushioning between the wearer's face and eyeglasses 10 without blocking the ventilation opening 42 of frame 14.

Assembly

Figure 6:
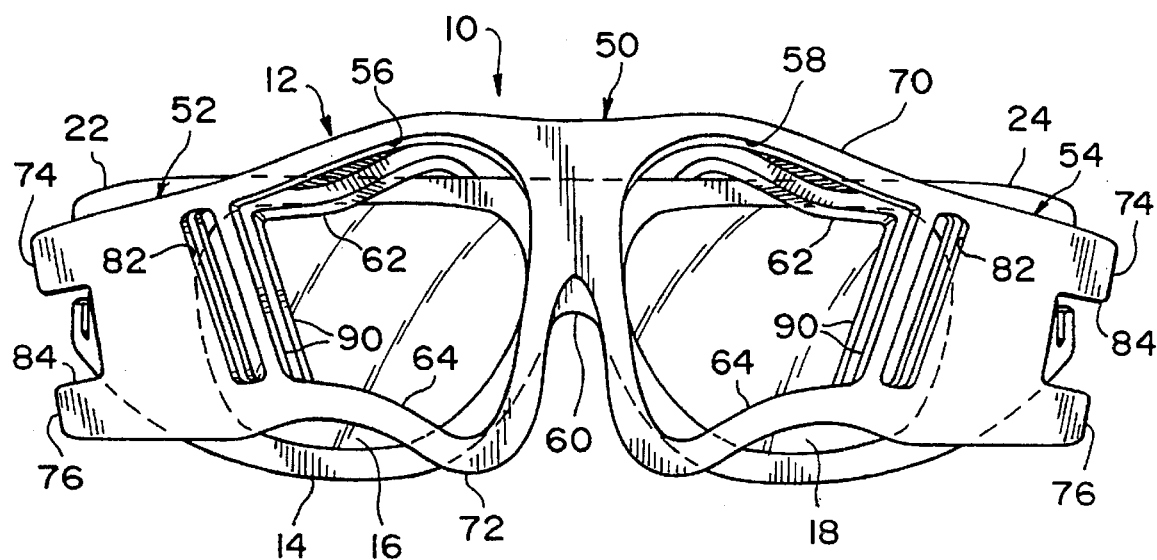
FIG. 6 is a front elevational view of the sports pad illustrated in FIGS. 1–4 with the sports pad partially covering the conventional prior art sports eyeglasses of FIG. 5.
Figure 7:
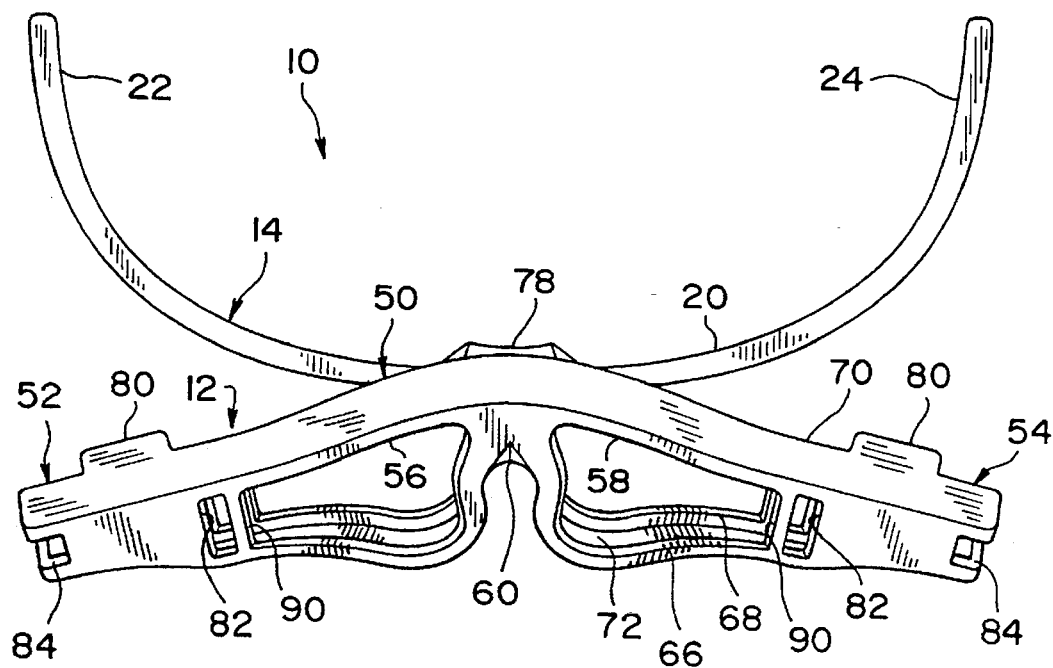
FIG. 7 is a top plan view of the sports pad and the conventional prior art sports eyeglasses illustrated in FIG. 6 with the sports pad partially covering the sports eyeglasses.

Pad 12 can be easily installed onto an existing frame such as frame 14 by stretching pad 12 over frame 14. In particular, the nose portion 60 of pad 12 is stretched, and one of the end portions 22 or 24 of frame 14 is then inserted in between front wall 66 and rear wall 68 of nose portion 60, until nose portion 60 of pad 12 rests in nose area 28 of frame 14 as shown in FIGS. 6 and 7. Since pad 12 is constructed of a resilient elastomeric material, nose portion 60 of pad 12 will snugly and firmly grip nose area 28 of frame 14.

Now, one of the end portions 52 or 54 is stretched longitudinally and slipped over the corresponding end portion 22 or 24 of frame 14 to position end portion 22 or 24 between front wall 66 and rear wall 68 of either end portion 52 or 54 of pad 12. Next, the other of the end portion 52 or 54 is likewise stretched longitudinally and slipped over the corresponding end portion 22 or 24 of frame 14 to position end portion 22 or 24 between front wall 66 and rear wall 68 of pad 12. Finally, pad 12 can now be moved and adjusted to correctly position pad 12 on frame 14.

If the pad 12 becomes worn out, or if it is desired to change the color of the pad 12, then the wearer need only reverse the assembly steps set forth above to remove pad 12 from frame 14. Of course, since pad 12 is very resilient, it is possible to assemble pad 12 onto frame 14 in a variety of ways by stretch pad 12 over frame 14.

Sports Eyewear 110 and Sports Pad 112

Referring initially to FIGS. 11–23, a pair of sports eyeglasses or eyewear 110 with a sports pad 112 coupled to a frame 114 of eyewear 110 is illustrated in accordance with a second embodiment of the present invention. Sports pad 112 is removably coupled to frame 114, and constructed of a soft, flexible, resilient rubber material which allows pad 112 to be stretched over frame 114.

Pad 112 covers substantially all exposed areas of frame 114 which can cause facial cutting when the eyeglasses 110 are struck by an object. Accordingly, the soft, rubber material of pad 112 is preferably transversely compressible to compress between the wearer's head and eyeglasses upon the eyeglasses 110 being struck by an object. In other words, pad 112 will prevent facial cutting from the hard frame 114 of eyeglasses 110 by absorbing a portion of the force exerted on the wearer's head from an object striking eyeglasses 110.

Preferably, pad 112 is injection molded from a thermoplastic elastomer as a one-piece, unitary member, i.e., constructed of one substantially homogeneous piece of material, not including separate but joined elements. Frame 114, on the other hand, is constructed of a hard material, and includes a pair of lenses 116 and 118 fixedly coupled thereto. Frame 114 also includes a front portion 120 for supporting lenses 116 and 118, and a pair of temple portions 122 and 124.

Figure 12:
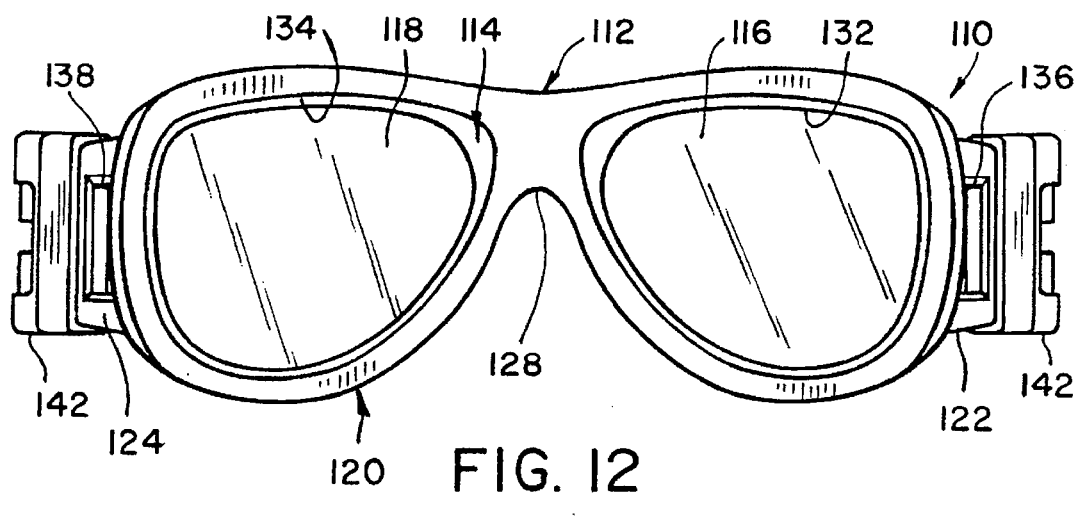
FIG. 12 is a front elevational view of a pair of conventional sports eyeglasses covered by a sports pad in accordance with a second embodiment of the present invention.
Figure 13:
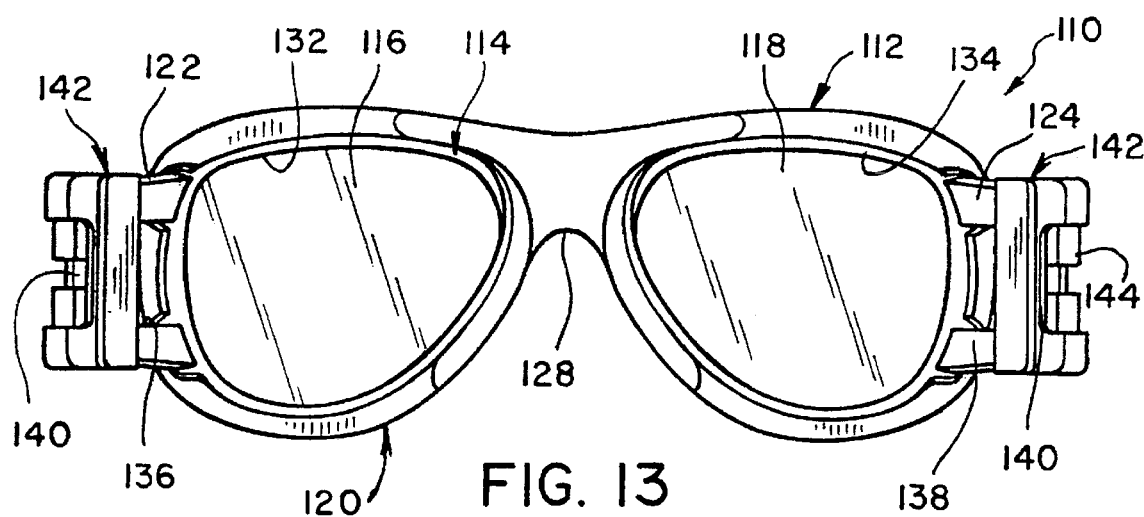
FIG. 13 is a rear elevational view of the eyeglasses and sports pad illustrated in FIG. 12 in accordance with the second embodiment of the present invention.
Figure 14:
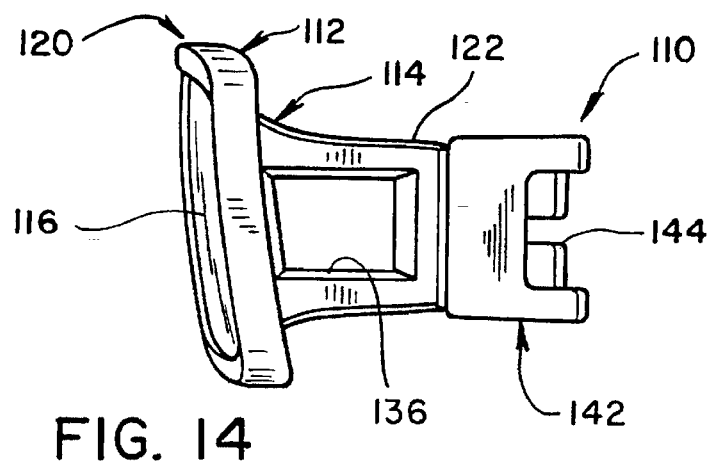
FIG. 14 is a right end elevational view of the eyeglasses and sports pad illustrated in FIGS. 12 and 13 in accordance with the second embodiment of the present invention.
Figure 15:
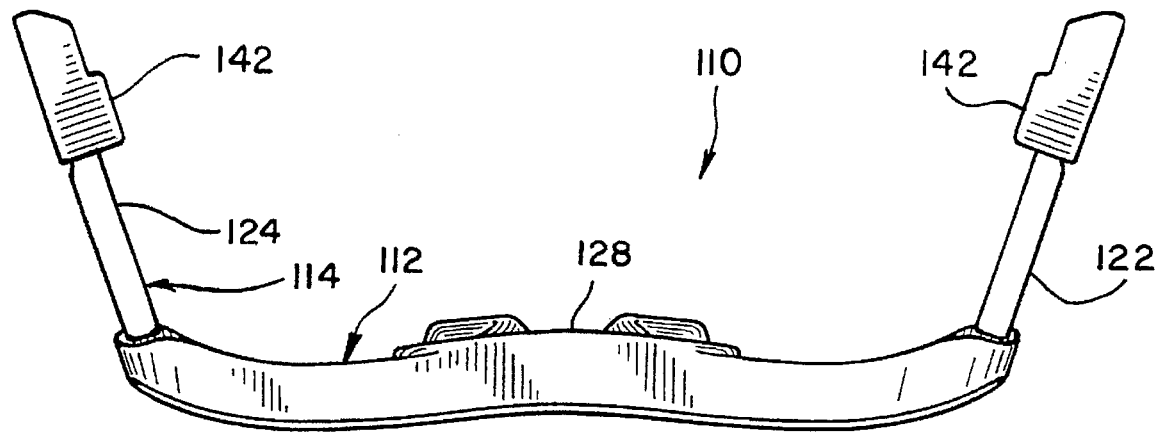
FIG. 15 is a top plan view of the eyeglasses and sports pad illustrated in FIGS. 12–14.
Figure 16:
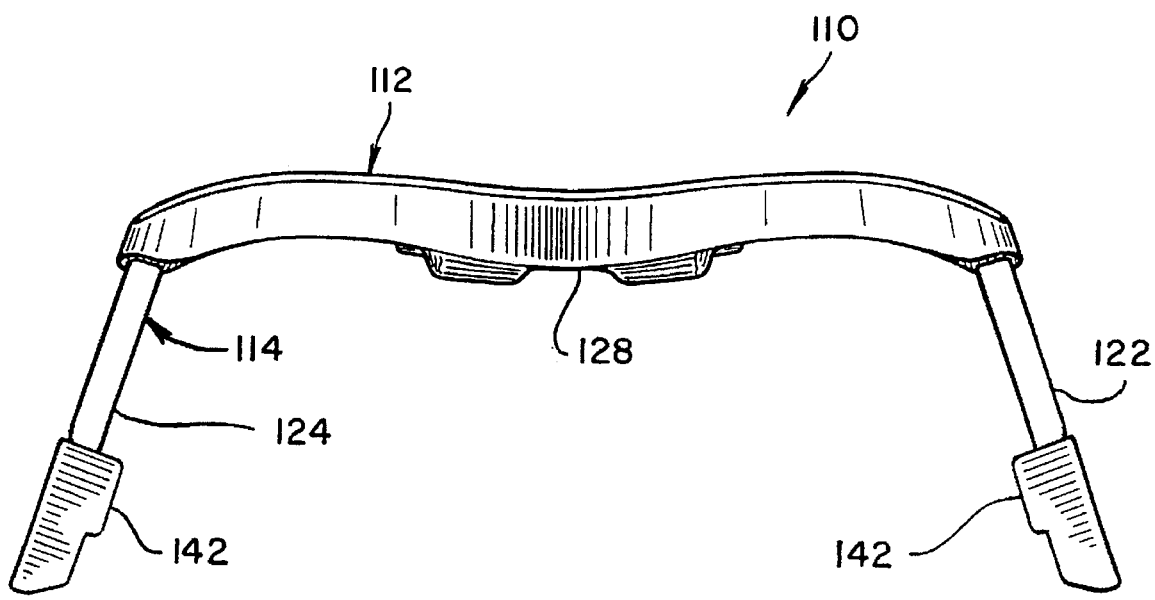
FIG. 16 is a bottom plan view of the eyeglasses and sports pad illustrated in FIGS. 12–15.

As seen in FIGS. 12–14, pad 112 substantially covers and encompasses all exposed areas of front portion 120 of frame 114 to prevent facial cutting from the hard frame 114 during impact with an object. A particularly suitable material for pad 112 is a very soft, elastomeric material with a durometer of approximately 13 ASTM A Shore to approximately 20 ASTM A Shore, such as the elastomer sold under the trademark Elastalloy which is an elastomeric derivative of the elastomer manufactured and sold by Shell Chemical Company under the trademark Kraton. Basically, the Elastalloy and Kraton elastomers are comprised of a block copolymer of butadiene, isoprene and styrene.

Pad 112 can be removably installed over frame 114 by stretching the resilient, rubber material of pad 112 over rigid frame 114 of eyeglasses 110. Accordingly, pad 112 can be easily replaced when worn out or changed to a different color pad. For example, pad 112 can be sold separately in a variety of colors, or sold as a kit containing a pair of protective eyeglasses 110 and a plurality of pads in a variety of colors.

Frame 114 is a conventional protective frame which is constructed of a hard, rigid material. It will be apparent to those skilled in the art from this disclosure that a variety of frames of other configurations can be used in conjunction with the present invention by modifying pad 112 to properly fit the particular configuration of the particular frames being used.

Preferably, front portion 120 and temple portions 122 and 124 are integrally molded as a one-piece, unitary frame. Front portion 120 is curved with a first temple portion or end 122 extending rearwardly from one end of front portion 120, and a second temple portion or end 124 extending rearwardly from the other end of front portion 120. The integrally molded frame 114 can be constructed of any material, but is advantageously constructed of a lightweight, moldable, shatterproof polymeric material, such as polycarbonate, propionate, cellulose acetate, nylon or butyrate. Frame 114 is illustrated in the figures as being constructed of an opaque material which can be any color. However, it will be apparent from this disclosure that frame 114 can be constructed of a transparent material which is either clear or colored.

Front portion 120 of frame 114 includes a centrally located nose area 128 forming a curved recess for receiving a wearer's nose, and a pair of apertures 132 and 134 for retaining lenses 116 and 118 therein. In particular, each of the apertures 132 and 134 preferably has a peripheral recess for retaining lenses 116 and 118, respectively, therein. Lenses 116 and 118 can be either refractive, i.e., prescription lenses, or non-refractive, i.e., non-prescription lenses, as needed. Of course, when using non-prescription lenses, lenses 116 and 118 can be integrally formed with frame 114 as a one-piece, unitary member with frame 114 and lenses 116 and 118 being formed of a clear or colored transparent plastic material. Alternatively, apertures 132 and 134 can be interconnected for receiving a single lens which is either refractive or non-refractive.

Optionally, temple portions 122 and 124 of frame 114 can have a pair of ventilation openings 136 and 138 to provide adequate circulation of air between frame 114 and the wearer's face. In particular, ventilation opening 136 is positioned between first temple portion 122 and front portion 120, and ventilation opening 138 is positioned between second temple portion 124 and front portion 120.

As particularly seen in FIGS. 12–16, first temple portion 122 and second end portion 124 are integrally molded with front portion 120 and extends approximately 1.5 inches to approximately 2.0 inches rearwardly from the ends of front portion 120. First end or temple portion 122 and second end or temple portion 124 are substantially identical, and thus, only first end portion 122 will be discussed and illustrated in detail.

First portion 122 has a strap slot 140 at its free end, and a temple pad 142. Strap slot 140 extends substantially vertically when eyeglasses 110 are worn by a wearer, and receives a conventional headband or strap (not shown) for securing the eyeglasses 110 to the wearer's head. An access slot 144 extends substantially perpendicularly from the midpoint of strap slot 140 to the free end of first temple portion 122 to provide easy installation of the headband or strap (not shown) into strap slot 140 in a conventional manner. Temple pads 142 are conventional elastomeric pads constructed of a resilient, compressible material such as the ones used for pad 112 as mentioned above.

Referring now to FIGS. 17–23, pad 112 is constructed as a one-piece, unitary member, and includes a front portion 150 for overlying and encompassing substantially all of the exposed areas of front portion 120 of frame 114. Accordingly, pad 112 fits over the hard, rigid material of frame 114 to provide a cushioning effect on the top, bottom, front and rear sides of frame 114 by substantially covering all of the exposed surfaces of front portion 120 of frame 114.

Pad 112 is dimensioned smaller than frame 114 so that pad 112 can be installed and removed by stretching pad 112 onto frame 114. The stretchability and resiliency of pad 112 permits a single pad 112 to be used on a plurality of different sizes of frames. In other words, a plurality of sizes of frames 114 can be fitted with the same pad 112 formed from a single mold due to the large degree of elasticity of pad 112.

Figure 17:
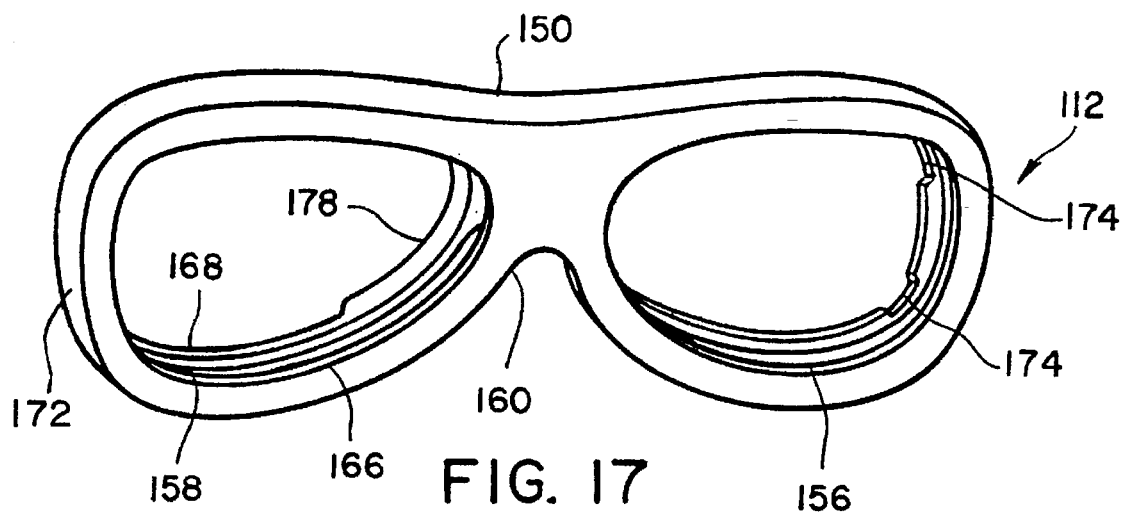
FIG. 17 is a front perspective view of the sports pad in its original, normal, unstretched state prior to being stretched over the sports pad eyewear frame as illustrated in FIGS. 12–16.
Figure 18:
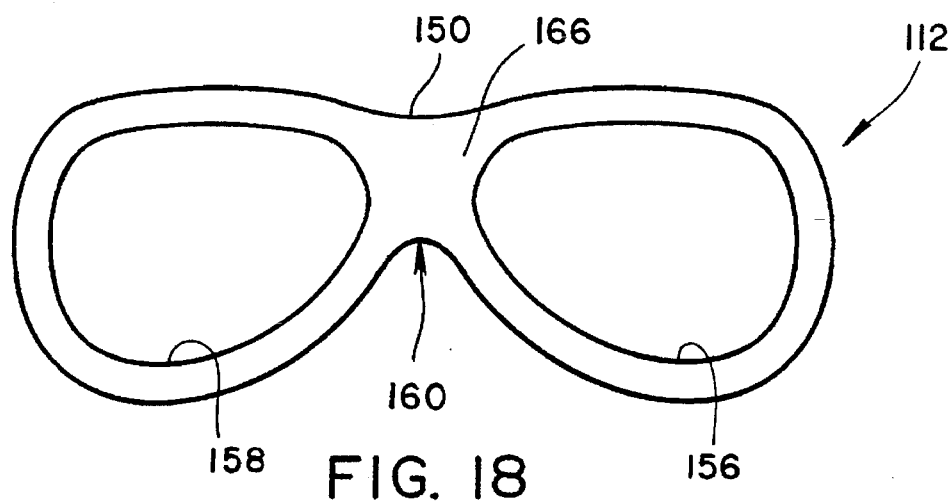
FIG. 18 is a front elevational view of the sports pad illustrated in FIG. 17 in its normal, original unstretched state prior to being stretched over the sports eyewear frames as illustrated in FIG. 12–16.
Figure 19:
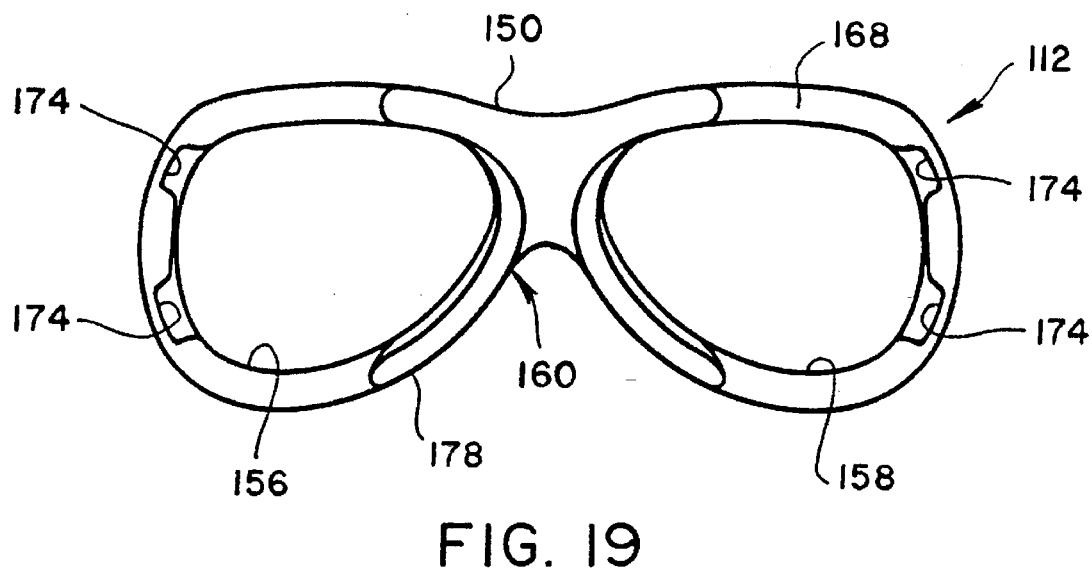
FIG. 19 is a rear elevational view of the sports pad illustrated in FIGS. 17 and 18 in its normal, original unstretched prior to being stretched over the sports eyewear frames as illustrated in FIGS. 12–16.
Figure 20:
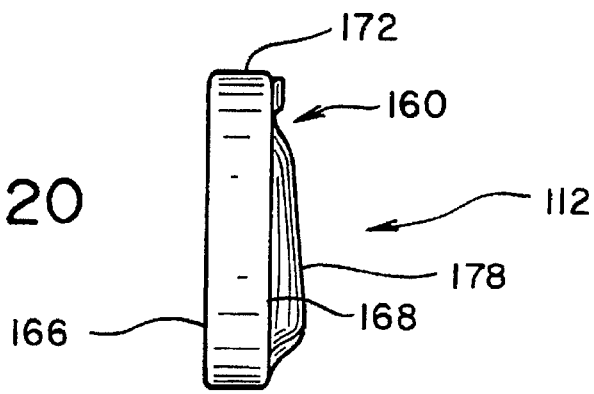
FIG. 20 is a right end elevational view of the sports pad shown in FIGS. 17–19 in its normal, original unstretched state prior to be stretched over the eyewear frames as illustrated in FIGS. 12–16.
Figure 21:
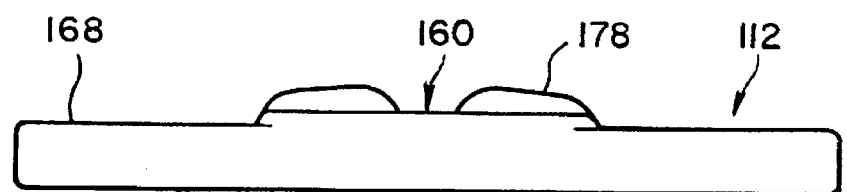
FIG. 21 is a top plan view of the sports pad illustrated in FIGS. 17–20 in its normal, unstretched state prior to being stretched over the eyewear frames shown in FIGS. 12–16.
Figure 22:
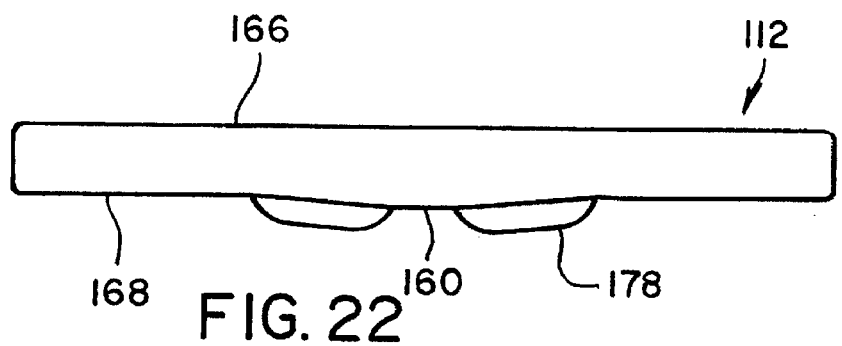
FIG. 22 is a bottom plan view of the sports pad illustrating FIGS. 17–21 in its normal, original unstretched state prior to be stretched over the sports eyewear frame as shown in FIGS. 12–16.
Figure 23:
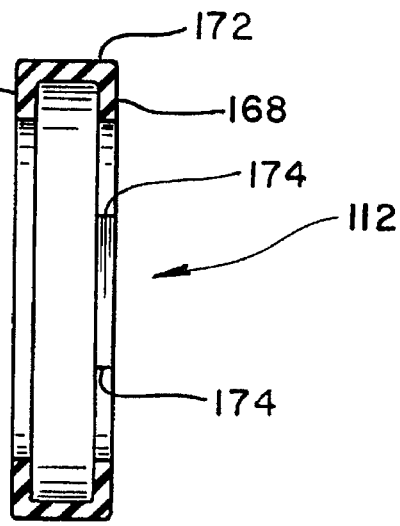
FIG. 23 is a cross-sectional view of the unstretched sports pad of FIGS. 17–22 taken along section line 19—19 of FIG. 19.
Figure 24:
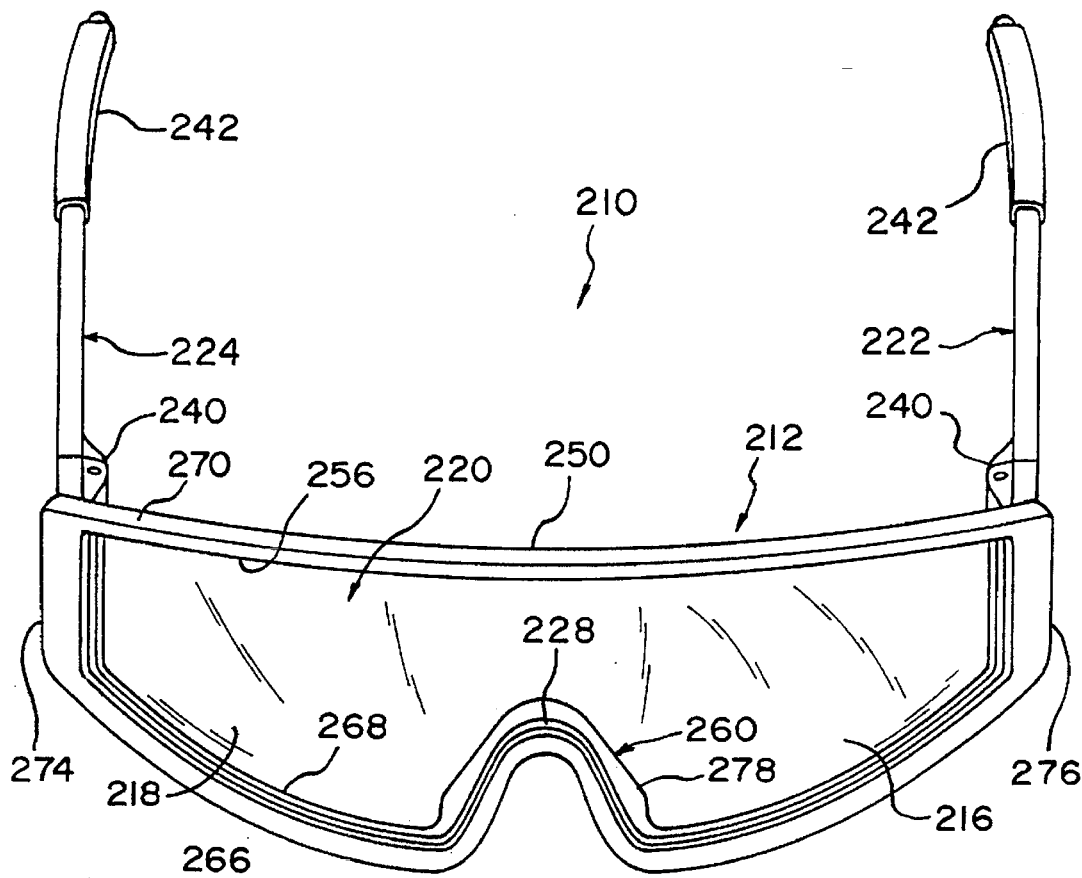
FIG. 24 is a front perspective view of a pair of sports eyeglasses or eyewear covered partially by a removable sports pad in accordance with a third embodiment of the present invention.
Figure 25:
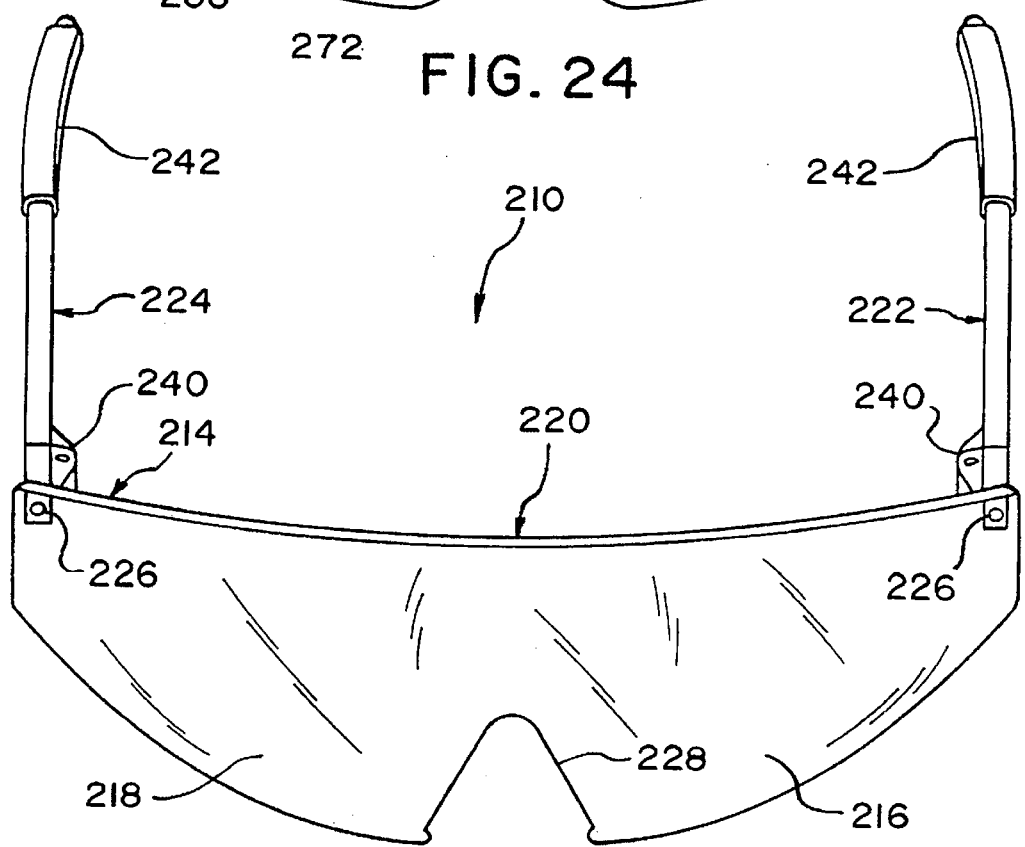
FIG. 25 is a front perspective view of the sports eyeglasses or eyewear illustrated in FIG. 24 with the sports pad removed.
Figure 26:
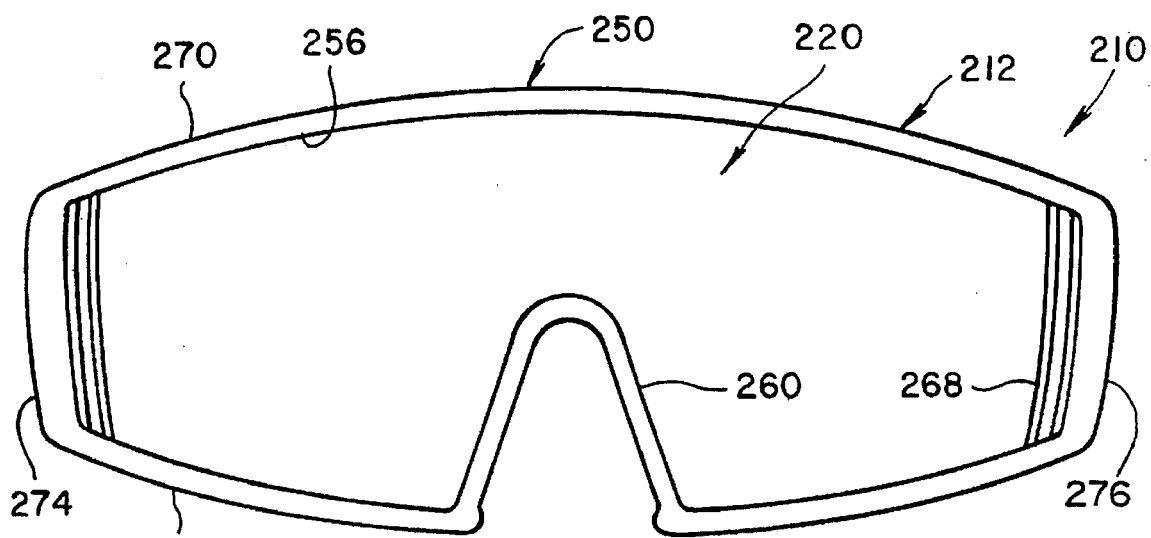
FIG. 26 is a front elevational view of the eyeglasses and sports pad illustrated in FIG. 24 in accordance with the third embodiment of the present invention.
Figure 27:
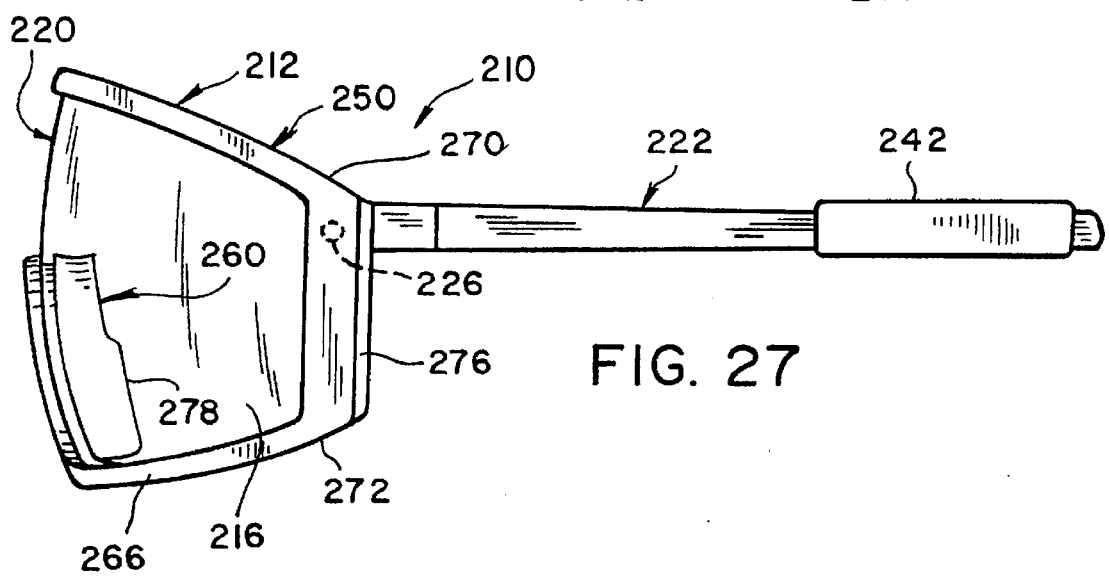
FIG. 27 is a right side elevational view of the eyeglasses and sports pad illustrated in FIGS. 24 and 26 in accordance with the present invention.
Figure 28:
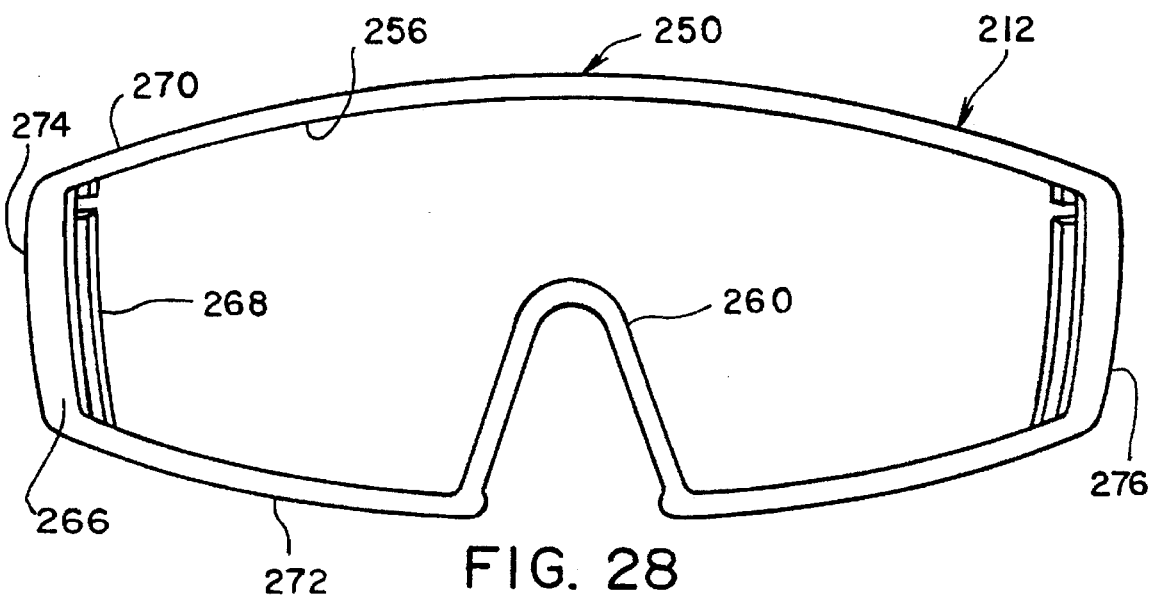
FIG. 28 is a front elevational view of the sports pad illustrated in FIGS. 24, 26 and 28 in its normal, original unstretched state prior to be stretched over the sports eyewear frames as illustrated in FIG. 24.
Figure 32:
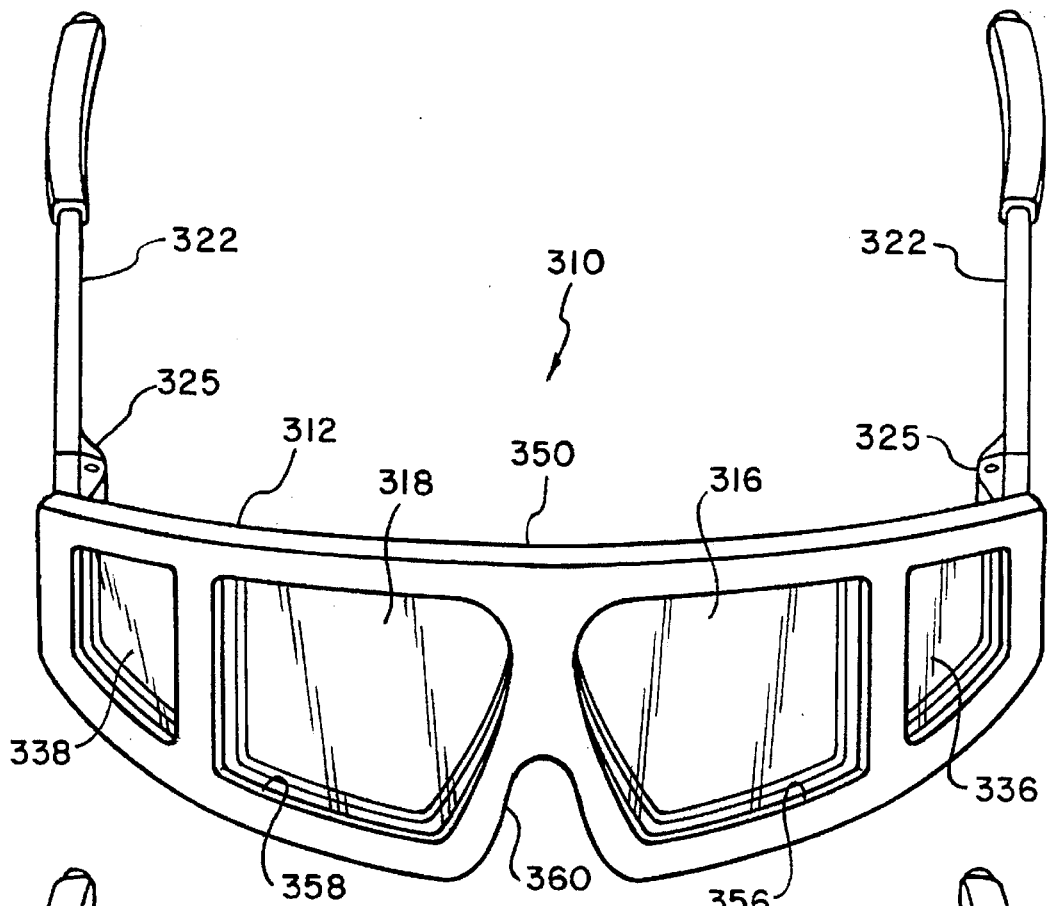
FIG. 32 is a front perspective view of a pair of sports eyeglasses or eyewear covered partially by a removable sports pad in accordance with a fourth embodiment of the present invention.
Figure 33:
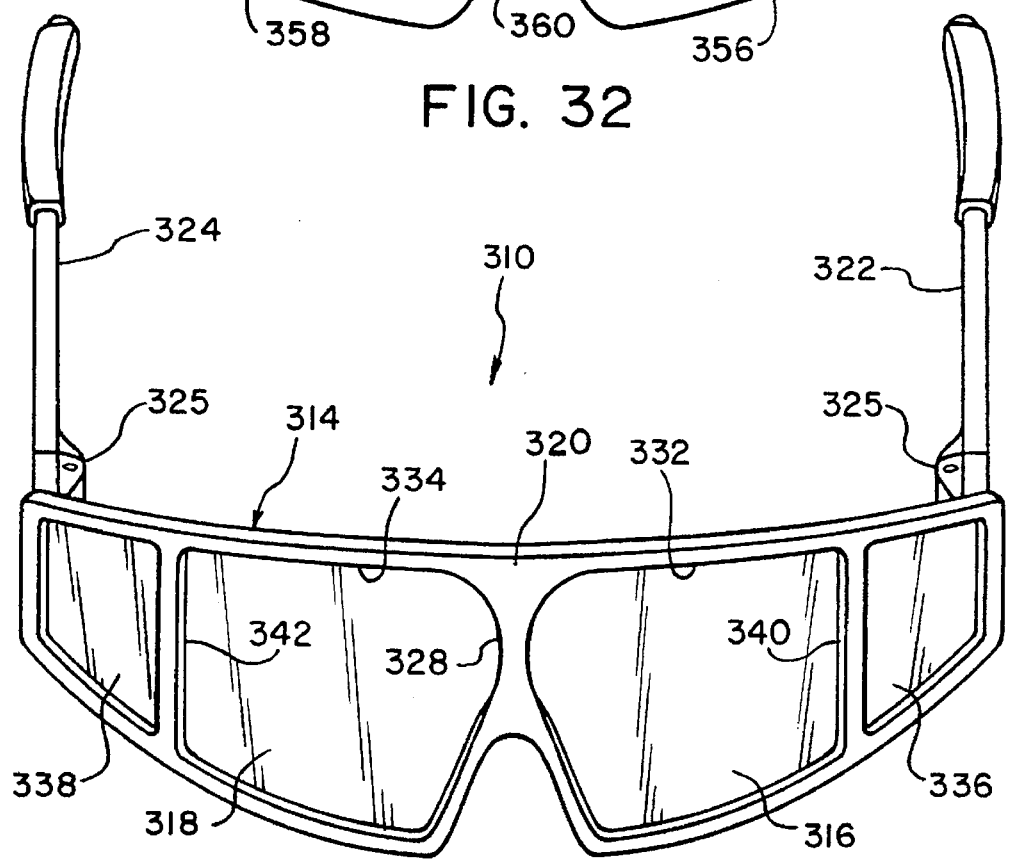
FIG. 33 is a front perspective view of the sports eyeglasses or eyewear illustrated in FIG. 32 with the sports pad removed.
Figure 34:
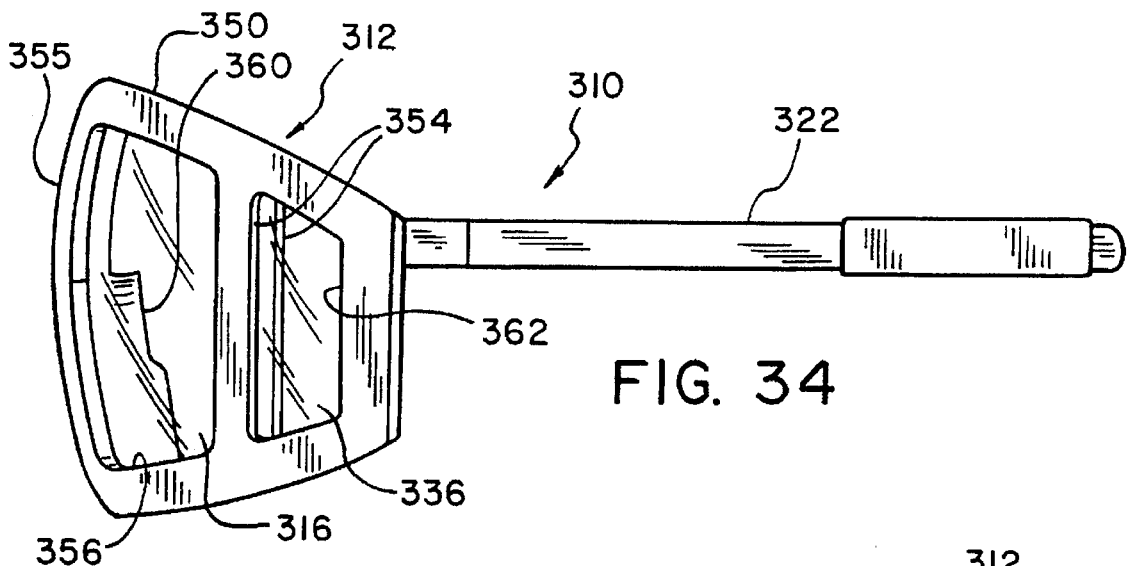
FIG. 34 is a right side elevational view of the eyeglasses and sports pad illustrated in FIG. 32 in accordance with the present invention.
Figure 35:
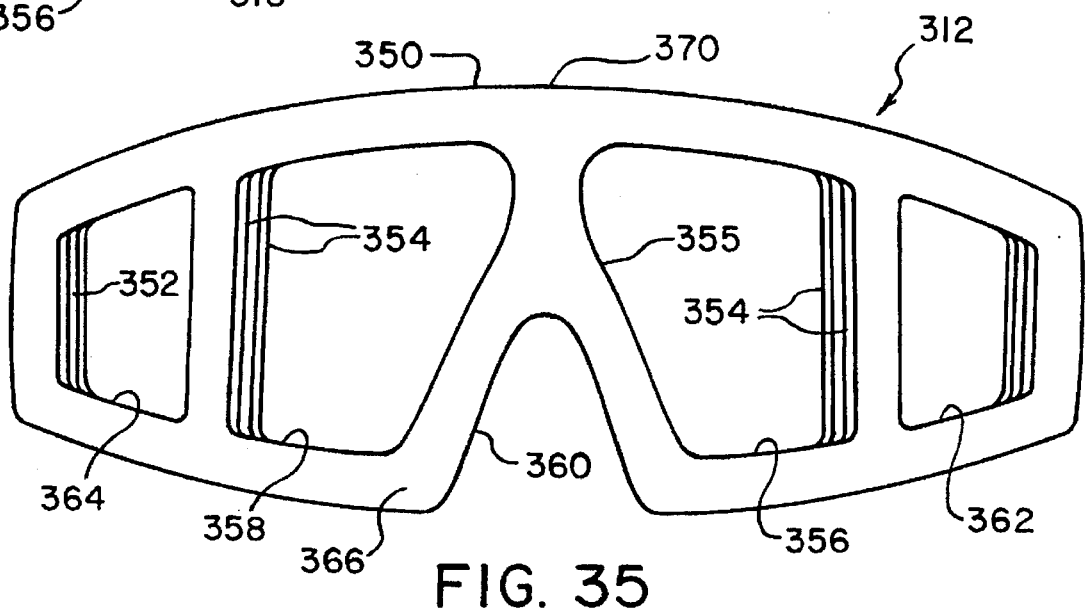
FIG. 35 is a front elevational view of the sports pad illustrated in FIGS. 32 and 34 in its normal, original unstretched state prior to be stretched over the sports eyewear frames as illustrated in FIG. 32.
Figure 36:
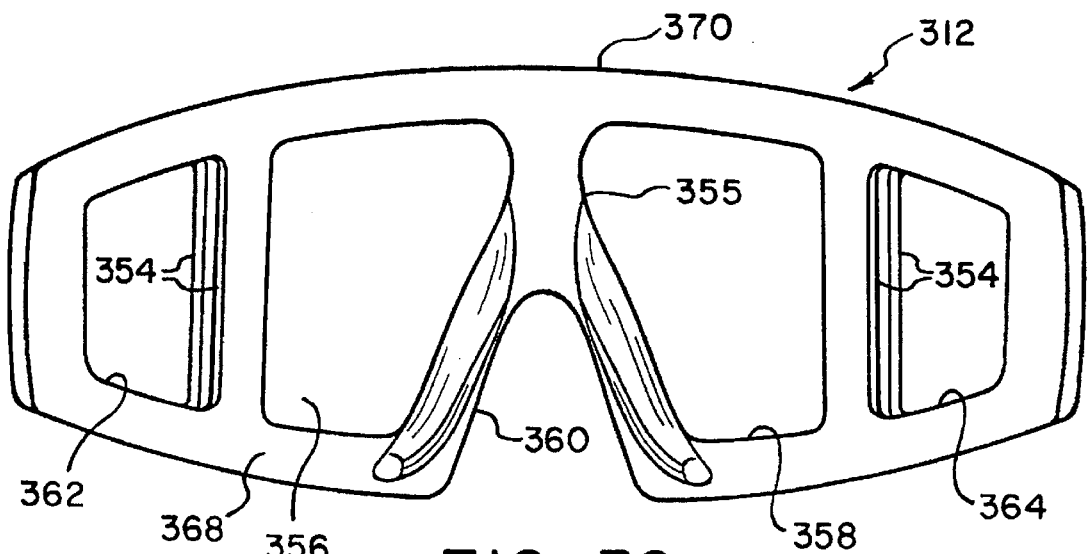
FIG. 36 is a rear elevational view of the sports pad illustrated in FIGS. 32, 34 and 35 in its normal, original unstretched state prior to be stretched over the sports eyewear frames as shown in FIG. 25.
Figure 38:
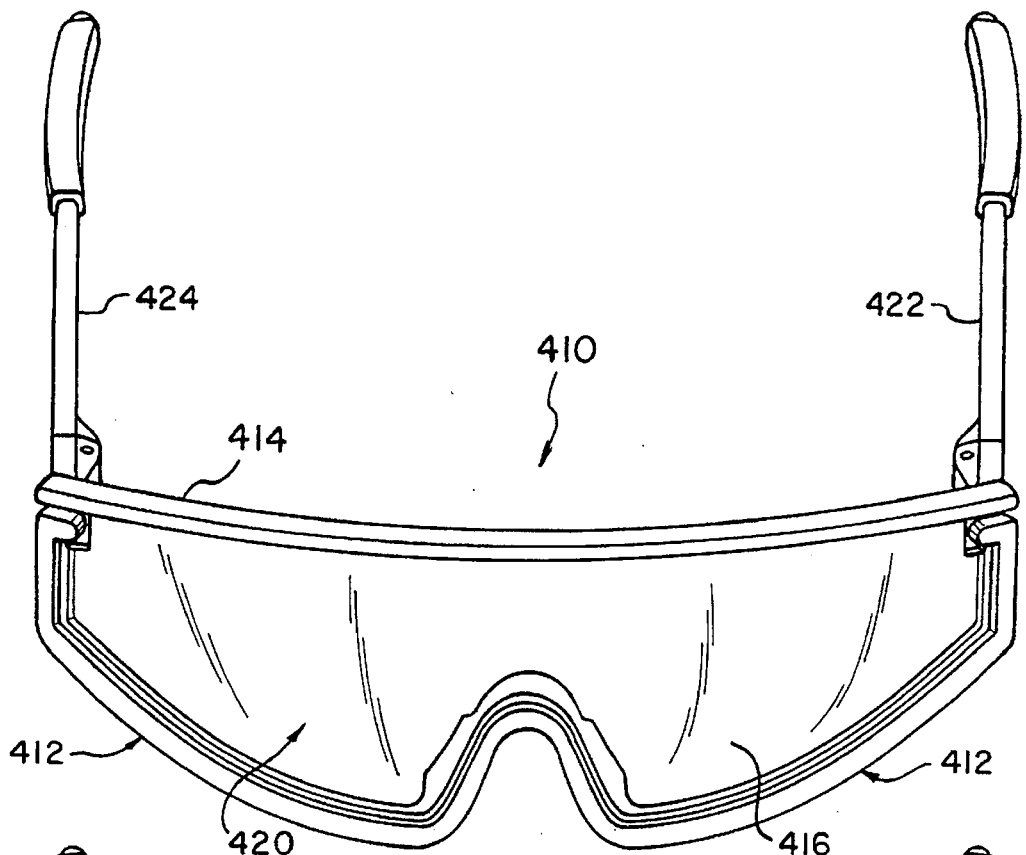
FIG. 38 is a front perspective view of a pair of sports eyeglasses or eyewear covered partially by a removable sports pad in accordance with a fifth embodiment of the present invention.
Figure 39:
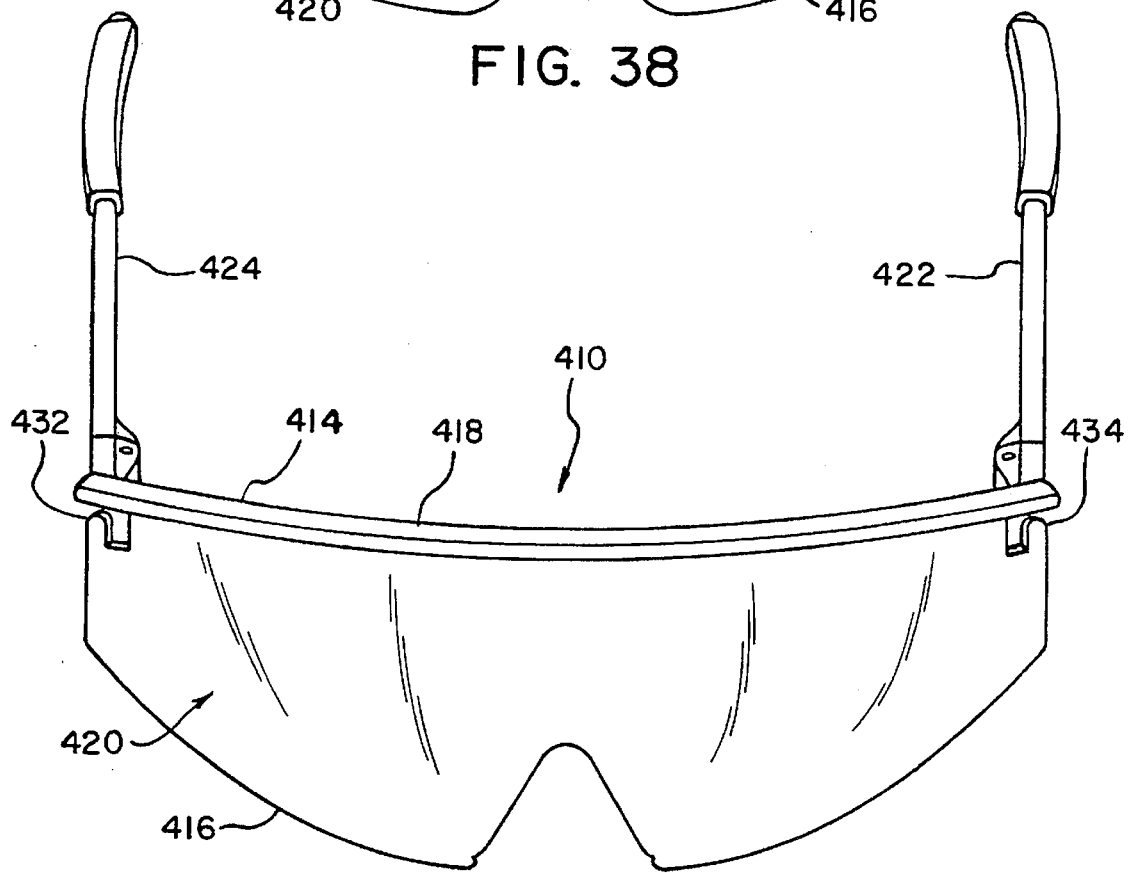
FIG. 39 is a front perspective view of the sports eyeglasses or eyewear illustrated in FIG. 38 with the sports pad removed.
Figure 40:
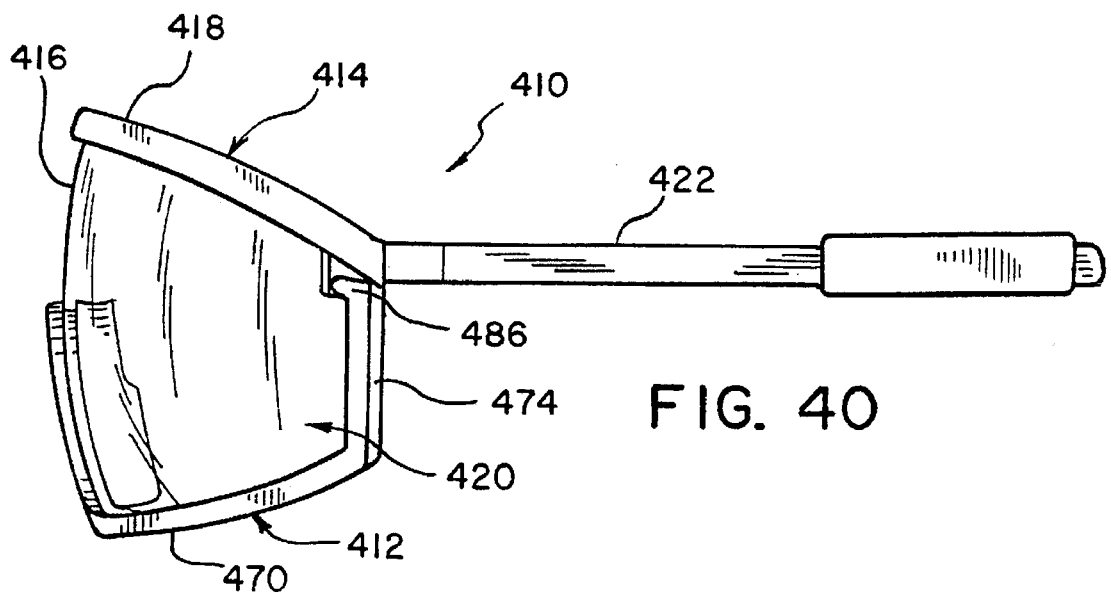
FIG. 40 is a right side elevational view of the eyeglasses and sports pad illustrated in FIG. 38 in accordance with the present invention.
Figure 41:
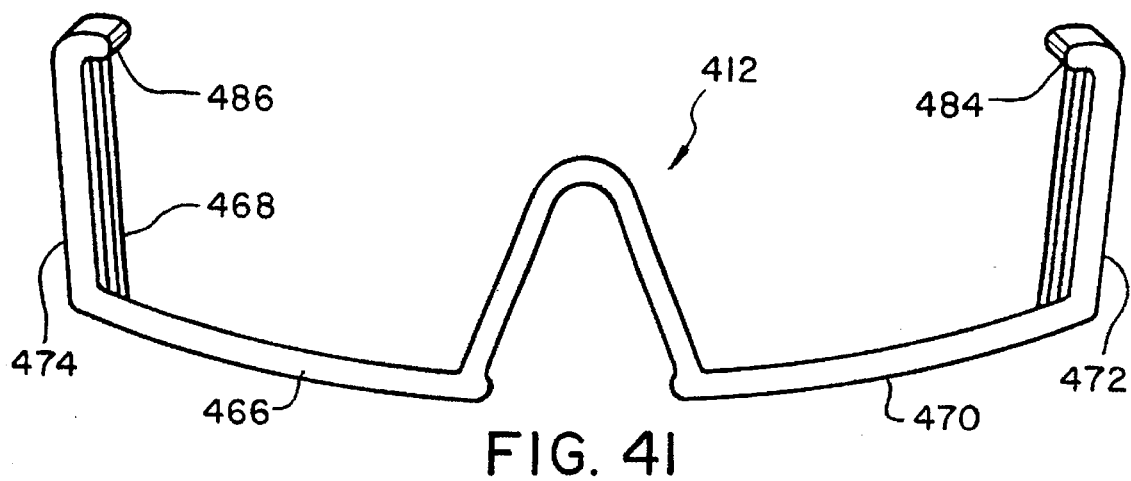
FIG. 41 is a front elevational view of the sports pad illustrated in FIGS. 38 and 40 in its normal, original unstretched state prior to be stretched over the sports eyewear frames as illustrated in FIG. 38.
Figure 42:
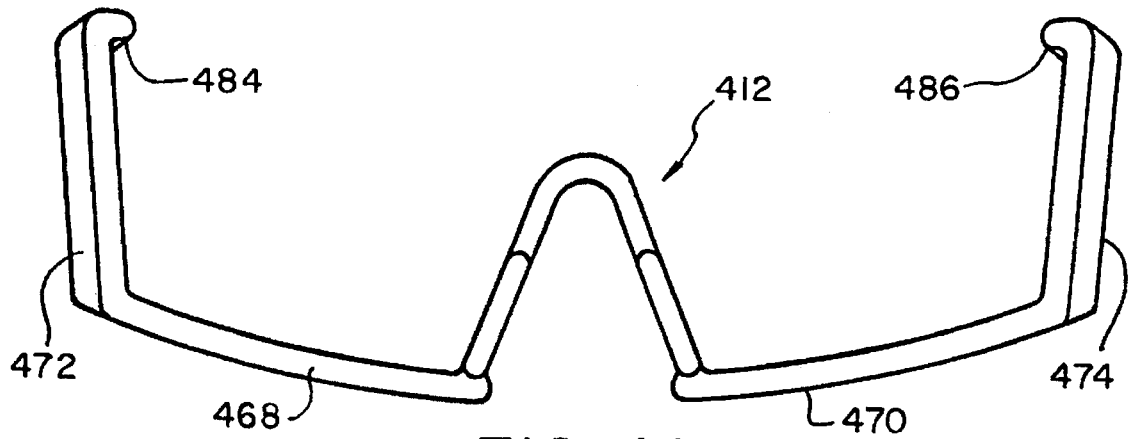
FIG. 42 is a rear elevational view of the sports pad illustrated in FIGS. 38, 40 and 41 in its normal, original unstretched state prior to be stretched over the sports eyewear frames as shown in FIG. 38.
Figure 37:
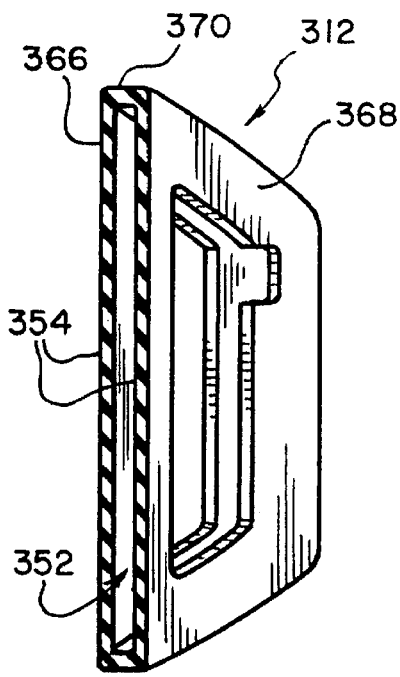
FIG. 37 is a cross-sectional view of the unstretched sports pad of FIGS. 32 and 34–36 taken along section line 37—37 of FIG. 36.
Figure 43:
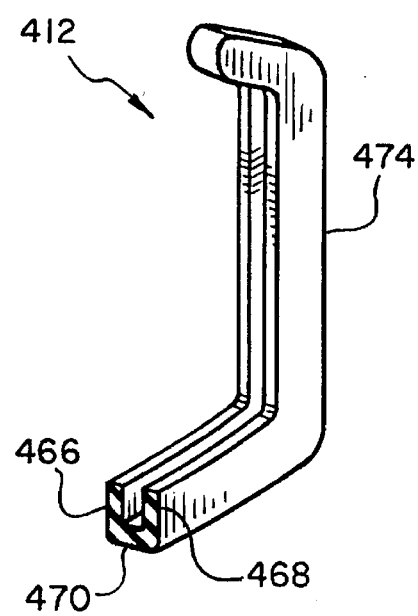
FIG. 43 is a cross-sectional view of the unstretched sports pad of FIGS. 38, and 40–42 taken along section line 43—43 of FIG. 38.
Figure 44:
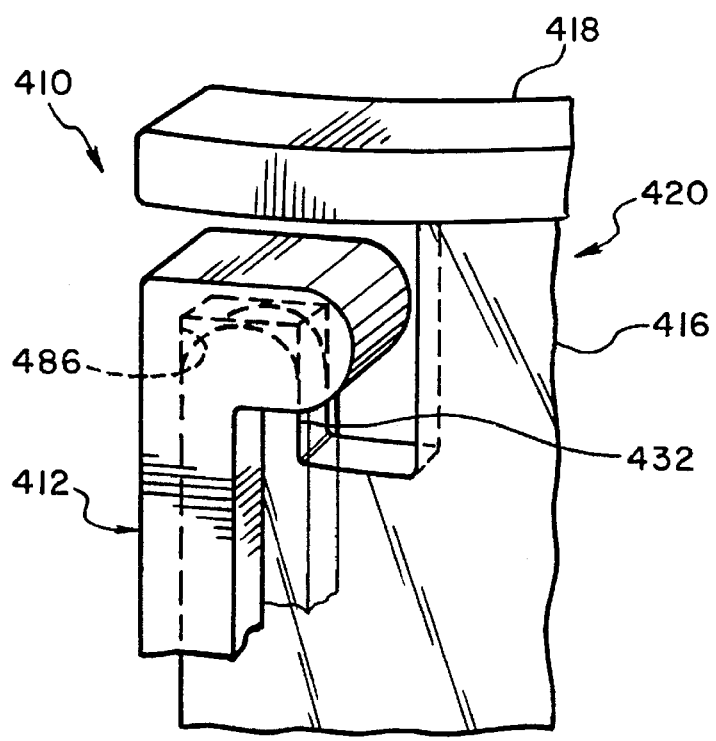
FIG. 44 is an enlarged, partial front elevational view of the interconnection of one end of the sports pad to the sports eyewear frames as illustrated in FIG. 38.

Front portion 150 of pad 112 includes a pair of lens apertures 156 and 158 and a nose portion 160 positioned between lens apertures 156 and 158. As shown in FIG. 17, for instance, each lens aperture 156 and 158 extends completely through the front and rear walls 156 and 158 of pad 112. Therefore, each lens aperture 156 and 158 comprises an aperture through the front wall 156 and an aperture through the rear wall 168. Apertures 156 and 158, in their normal unstretched state, are preferably uniformly smaller than apertures 132 and 134 of frame 114 to provide a secure fit about the frame 114.

As seen in FIGS. 17–23, front portion 150 of pad 112 is formed by a front wall 166, a rear wall 168 and a continuous peripheral wall 172. Front wall 166, rear wall 168 and peripheral wall 172 form a U-shaped peripheral channel for receiving the peripheral edge of front portion 120. In other words, top peripheral wall 170 and bottom peripheral wall 172 extend substantially perpendicularly between front wall 166 and rear wall 168 for engaging the upper and lower edges of frame 114, respectively. Pad 112 is elastically stretched over front portion 120 and thereby retained on frame 114 to limit shifting of pad 112 on frame 114. Rear wall 168 has four cutouts 174 for accommodating portions of temple portions 122 and 124 so as to provide a tight fit therebetween.

When pad 112 is in its unstressed state as shown in FIGS. 17–22, front wall 166 is parallel to and spaced from rear wall 168 to receive frame 114 therebetween. Preferably, the distance between front wall 166 and rear wall 168 is slightly greater than the thickness of frame 114 in its unstressed state. Of course, the distance between front wall 166 and rear wall 168 can be smaller than or the same size as the thickness of frame 114. Preferably, when pad 112 is stretched onto frame 114, the distance between rear front wall 166 and rear wall 168 will decrease to elastomerically grip frame 114.

Nose portion 160 includes a nose cushion 178 which extends outwardly from rear wall 168 between apertures 156 and 158. Nose cushion 178 provides additional padding between the wearer's nose and the nose area 128 of frame 114. In particular, nose cushion 178 is contoured to engage the wearer's nose.

Sports Eyewear 210 with Sports Pad 212

Referring now to FIGS. 24–31, a pair of sports eyeglasses or eyewear 210 with a sport pad 212 coupled to its frame 214 of eyewear 210 is illustrated in accordance with a second embodiment of the present invention.

Sports pad 212 is removably coupled to frame 214, and constructed of a soft, flexible, resilient rubber material which allows pad 212 to be stretched over frame 214. Pad 212 covers substantially all exposed edges of the front portion 220 of frame 214 so as to reduce facial cutting when the eyewear 210 is struck by an object. Accordingly, the soft, rubber material of pad 212 is preferably transversely compressible to compress between the wearer's head and the eyewear frames upon the eyewear frames 214 being struck by an object. In other words, pad 214 will prevent facial cutting from the hard edges of frame 214 of eyeglasses 210 by cushioning and absorbing a portion of the force exerted on the wearer's head from the striking object.

Preferably, pad 212 is injection molded from a thermal plastic elastomer as a one-piece, unitary member, i.e., constructed of one substantially homogenous piece of material, not including separate but joined elements. Frame 214, on the other hand, is constructed of a hard, substantially rigid material. More specifically, frame 214 includes a pair of lens panes 216 and 218 formed as an integral lens forming a curved front portion 220, and a pair of temple portions 222 and 224 rigidly coupled to the lens or front portion 220 of frame 214 by rivets 226.

Pad 212 substantially covers and encompasses the peripheral edge of the lens or front portion 220 of frame 214 to prevent facial cutting the edge of front portion 120 during impact with an object. A particularly suitable material for pad 212 is a very soft, elastomeric material with a durometer of approximately 13 ASTM A Shore to approximately 20 ASTM A Shore, such as the elastomer sold under the trademark Elastalloy which is an elastomeric derivative of the elastomeric manufactured and sold by Shell Chemical Company under the trademark Kraton. Basically, the Elastalloy and Kraton elastomers are comprised of a block copolymer of butadiene, isoprene and styrene.

Pad 212 can be removably installed over the peripheral edge of front portion 220 of frame 214 by stretching the resilient, rubber material of pad 212 over the rigid lens or front portion 220 of eyewear 210. Accordingly, pad 212 can be easily replaced when worn out or changed to a different color pad. For example, pad 212 can be sold separately in a variety of colors, or sold as a kit containing a pair of protective eyeglasses 210 and a plurality of pads 212 in a variety of colors.

While front portion 220 is a frameless lens, it will be apparent to those skilled in the art from this disclosure that front portion 220 can be framed and can have a variety of frame configurations. Of course, pad 212 would need to be modified to accommodate the various changes in the configuration of the eyewear 210 as seen in the other embodiments disclosed herein.

Preferably, frame 214 of this embodiment utilizes a one-piece frame front or lens 220 with integral lens panes 216 and 218 and separate temple portions 222 and 224 coupled to lens or front portion 220 by rivets Preferably, both lens or front portion 220 and temple portions 222 and 224 are injection molded from a shatterproof polymeric material, such as polycarbonate, propionate, cellulose acetate, nylon or butyrate. Of course, front needs to be constructed of a transparent material which is either clear or colored, while temple portion 222 and 224 can be constructed of either transparent or non-transparent material.

Front portion or lens 220 of frame 214 includes a centrally located nose area 228 forming a curved recess for receiving a wearer's nose. Of course, frame front can have a variety of shapes.

Temple portions 222 and 224 are substantially identical, and are relatively conventional. In particular, temple portions 222 and 224 have a hinge 240 for pivoting temple portions 222 and 224 inwardly in a closed position for storage. Temple portions 222 and 224 also preferably includes a resilient, compressible pad 242 which is frictionally retained on temple portions 222 and 224. Temple pads 242 are preferably constructed of substantially the same material as pad 212 as discussed above. Since temple portions 222 and 224 are relatively conventional, temple portions 222 and 224 will not be discussed in detail herein.

Pad 212 is constructed as one-piece, unitary member, and includes a front portion 250 for overlying and encompassing substantially the entire exposed peripheral edge of lens of front portion 220 of frame 214. Pad 212 is dimensioned slightly smaller than lens or front portion 220 so that pad 212 can be installed and removed by stretching pad 212 onto frame front 220. The stretchability and resiliency of pad 212 permits a single pad 212 to be worn on a plurality of different size of frames. In other words, a plurality of size of frames 214 can be fitted with the same pad 212 formed from a single mold due to the large degree of elasticity of pad 212.

Front portion 250 of pad 212 includes a lens aperture 256 and a nose portion 260 positioned midway between lens aperture 256. Front portion 250 of pad 212 is formed by a front wall 266, a rear wall 268, a top peripheral wall 270, a bottom peripheral wall 272 and a pair of end peripheral walls 274 and 276. Peripheral walls 270, 272, 274 and 276 are continuous with each other and together with walls 266 and 268 form a continuous U-shaped peripheral channel. When pad 212 is in its unstretched state, front wall 266 is parallel to and spaced from rear wall 268 to receive frame 214 therebetween. Preferably, the distance between front wall 266 and rear wall 268 is slightly greater than the thickness of frame 214 in its unstressed or unstretched state. Of course, the distance between front wall 266 and rear 268 can be smaller than or the same size as the thickness of the frame front 220. Preferably, when pad 212 is stretched onto frame 214, the distance between front wall 266 and rear wall 268 will decrease slightly to elastomerically grip the lens or front portion 220 of frame 214. Peripheral wall 270 extends substantially perpendicularly between front wall 266 and rear wall 268 for forming an annular channel for receiving the peripheral edge of lens or front portion 220 of frame 214.

Nose portion 260 includes a nose cushion 278 which extends outwardly from rear wall 268 midway between lens aperture 256. Nose cushion 278 provides additional padding between the wearer's nose and the nose area 228 of frame 214. In particular, nose cushion 278 is contoured to engage the wearer's nose.

Eyewear 310 with Sports Pad 312

Referring now to FIGS. 32–37, a pair of sports eyeglasses or eyewear 310 with a sports pad 312 coupled to a frame 314 of eyewear 310 is illustrated in accordance with a fourth embodiment of the present invention. Sports pad 312 is removably coupled to frame 314, and constructed of a soft, flexible, resilient rubber material which allows pad 312 to be stretched over frame 314. Eyewear 310 and sports pad 312 are similar to eyewear 210 and sports pad 212. Accordingly, only the differences between these two embodiments will be discussed in detail herein. More specifically, eyewear 310 has been modified to include a frame front 320 with a pair of lenses 316 and 318 formed separately from the frame front as well as a pair of side windows 336 and 338 which are also formed separately from frame front 320. Accordingly, sports pad 312 has been modified to include additional portions to overlie the front portion 320 of frame 314.

In particular, pad 312 covers substantially all exposed areas of front portion 320 of frame 314 so that the front portion 320 of frame 314 cannot be seen from a distance. Preferably, pad 312 is injection molded from thermal plastic elastomer as a one-piece, unitary member in the same manner as the sports pads of the other embodiments discussed herein.

Frame 314 is a protective frame which is constructed of a hard, rigid material. It will be apparent to those skilled in the art from this disclosure that a variety of frame configurations can be used in conjunction with the present invention by modifying pad 312 to properly fit the particular configuration of the particular frame being used.

Preferably, front portion 320 is integrally molded as a one-piece, unitary member with temple portions 322 and 324 rigidly coupled to the ends of frame front 320 by hinges 325 which are fastened to front portion 320 of frame 312.

Front portion 320 of frame 312 includes a centrally located nose area or rib 328 forming a curved recess for receiving a wearer's nose, and a pair of separate lens apertures 332 and 334 for retaining lenses 316 and 318 therein. In particular, each of the apertures 332 and 334 preferably has a peripheral recess for retaining lenses 316 and 318, respectively, therein. Lenses 316 and 318 can be either refractive, i.e., prescription lenses, or non-refractive, i.e., non-prescription lenses, as needed. Of course, when using non-prescription lenses, lenses 316 and 318 can be integrally formed with front portion 320 as a one-piece, unitary member.

Optionally, front portion 320 of frame 314 can have a pair of windows 336 and 338 which are constructed of a transparent material. In particular, lens apertures 332 and 334 are separated from windows 336 and 338 by ribs 340 and 342, respectively.

Pad 312 is constructed as a one-piece, unitary member, and includes a front portion 350 for overlying and encompassing substantially all of the exposed areas of front portion 320 of frame 314. Pad 312 is dimensioned slightly smaller than frame 314 so that pad 312 can be installed and removed by stretching pad 312 onto frame 314. Preferably, the outline or overall shape of pad 312 is slightly larger than the outline or overall shape of front portion 320 of frame 314 when stretched onto the frame so as to completely cover front portion 320 and the peripheral areas of lenses 316 and 318 and windows 336 and 338. In particular, front portion 350 of pad 312 includes a pair of lens apertures 356 and 358, a nose portion 360 positioned between lens apertures 356 and 358, and a pair of window apertures 362 and 364. In particular, front portion 350 includes an annular channel shaped portion 352 for surrounding and covering the peripheral portions of front portion 320, ribbed portions 354 for covering ribs 340 and 342, and a central rib portion 355 for covering nose rib 328.

Accordingly, front portion 350 of pad 312 is formed by a front wall 366 overlying the front portions of front portion 320 of frame 314, a rear wall 368 overlying the rearwardly facing portions of front portion 320 of frame 314, and a peripheral wall overlying the peripheral edge of front portion 320 of frame 314.

Sports Eyewear 410 with Sports Pad 412

Referring now to FIGS. 38–44, a pair of sports eyeglasses or eyewear 410 with a sports pad 412 coupled to a frame 414 of eyewear 410 is illustrated in accordance with the present invention. Eyewear 410 and sports pad 412 are substantially identical to eyewear 210 and sports pad 212, except that front portion 420 has been modified to include an upper frame front 418 with temple portions 422 and 424 hingedly coupled to thereto and sports pad 412 has been modified to only extend along the bottom and side peripheral edges of front portion 420. Accordingly, eyeglasses 410 and sports pad 412 will not be discussed in detail herein.

Frame 414 includes frame front 418 and pair of temple portions 422 and 424 which are hingedly coupled to front portion 420 as well as a lens 416 having a pair of integral lens panes. Frame front 418 fixedly coupled along the upper edge of lens 416. Accordingly, lens 416 is frameless along its two end edges and its bottom edge and thus, sports pad 412 overlies the side peripheral edges and the bottom peripheral edge of lens 416.

Lens 416 includes a pair of protrusions 432 and 434 formed adjacent frame front 418 for coupling sports pad 412 thereto. In particular, each of the protrusions 432 and 434 are located at the upper end corners of the lens adjacent the frame front for a 418. Protrusion 432 and 434 acts as hooks for receiving a portion of sports pad 412 thereon as discussed below.

Sports pad 412 includes a front wall 466, a rear wall 468, a bottom peripheral wall 470 and a pair of end peripheral walls 472 and 474. Front wall 466, rear wall 468, bottom peripheral wall 470 and end peripheral walls 472 and 474 form a U-shaped channel for receiving the bottom and end peripheral edges of lens 416. The rear wall 468 has a nose pad 480 extending rearwardly therefrom for providing additional cushioning between the wearer's face and the lens 416.

The upper ends of the U-shaped channel of pad 412 are closed off to form a pair of pockets 484 and 486 for hooking onto protrusions 432 and 434 of lens 416. In other words, the peripheral edges of lens 416 are inserted into the U-shaped channel formed by the walls of pad 412 and the pad is then stretched so that the end pockets 484 and 486 hook onto the protrusions 432 and 434 of lens 416.

While several embodiments have been chosen to illustrate the invention, it will be understood by those skilled in the art that various changes and modifications can be made herein without departing from the scope of the invention as defined in the appended claims.

What is claimed is:

1. A removable sports pad for covering at least certain exposed peripheral edges of eyewear with a front portion and a pair of temple portions, comprising:

a front wall for removably overlying certain forwardly facing areas of said eyewear;

a rear wall spaced from said front wall for removably overlying certain rearwardly facing areas of said eyewear and for removably receiving said eyewear therebetween;

a peripheral wall coupled between said front and rear walls for removably overlying certain peripheral edges of said eyewear; and first and second lens apertures being formed in said pad and extending through said pad, said rear wall further comprising a nose portion positioned between said first and second lens apertures, each of said front, rear and peripheral walls of said pad being constructed of a soft, stretchable, resilient material for removably retaining said pad on said eyewear and being shaped to overlie at least portions of the peripheral edges of the eyewear along its lens.

2. A removable sports pad according to claim 1, wherein said front wall, said rear wall and said peripheral walls are integrally formed as a one-piece, unitary member.

3. A removable sports pad according to claim 1, wherein said nose portion includes a nose cushion, said nose cushion being part of said rear wall.

4. A removable sports pad according to claim 2, wherein said front wall, said rear wall and said peripheral wall form a substantially U-shaped channel with said peripheral wall extending substantially perpendicular to said front and rear walls.

5. A removable sports pad according to claim 2, wherein said rear wall includes at least two cutouts for accommodating the temple portions of the eyewear.

6. A removable sports pad according to claim 2, wherein said peripheral wall extends substantially around the peripheral edge of the front portion of the eyewear.

7. A removable sports pad according to claim 6, wherein said front wall and said rear wall have substantially the same outline when viewed in elevation.

8. A removable sports pad according to claim 3, wherein each of said first and second lens apertures being formed by front and rear wall apertures.

9. Sports eyewear for eye protection, comprising:

a substantially rigid eyewear frame having a front portion with at least one lens, a first temple portion being coupled to a first end of said front portion of said frame, and a second temple portion being coupled to a second end of said front portion of said frame; and a soft, elastomeric pad removably coupled to said frame for covering at least certain exposed areas of said frame, said pad including a front wall for removably overlying certain forwardly facing areas of said eyewear;

a rear wall spaced from said front wall for removably overlying certain rearwardly facing areas of said eyewear and for removably receiving said eyewear therebetween;

a peripheral wall coupled between said front and rear walls for removably overlying certain peripheral edges of said eyewear; and first and second lens apertures being formed in said pad and extending through said pad, said rear wall further comprising a nose portion positioned between said first and second lens apertures, each of said front, rear and peripheral walls of said pad being constructed of a soft, stretchable, resilient material for removably retaining said pad on said eyewear and being shaped to overlie at least portions of the peripheral edges of the eyewear along said at least one lens.

10. Sports eyewear according to claim 9, wherein said pad is formed as a one-piece, unitary member which is separate from said eyewear frame.

11. Sports eyewear according to claim 10, wherein said front portion includes a frame front with a pair of lenses coupled thereto; and each of said first and second apertures being formed by front and rear wall apertures.

12. Sports eyewear according to claim 11, wherein said rear wall of said pad includes at least two cutouts for accommodating said first and second temple portions.

* * * * *